US012151021B2

(12) United States Patent
Grattoni et al.

(10) Patent No.: US 12,151,021 B2
(45) Date of Patent: *Nov. 26, 2024

(54) IMPLANTABLE NANOCHANNEL DELIVERY DEVICES

(71) Applicant: THE METHODIST HOSPITAL SYSTEM, Houston, TX (US)

(72) Inventors: Alessandro Grattoni, Houston, TX (US); Edward Brian Butler, Houston, TX (US); Ganesh Palapattu, Ann Arbor, MI (US)

(73) Assignee: THE METHODIST HOSPITAL SYSTEM, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,304

(22) Filed: Feb. 27, 2023

(65) Prior Publication Data

US 2023/0310310 A1     Oct. 5, 2023

Related U.S. Application Data

(63) Continuation of application No. 16/879,984, filed on May 21, 2020, now Pat. No. 11,590,072, which is a continuation of application No. 15/574,185, filed as application No. PCT/US2016/032658 on May 16, 2016, now abandoned.

(60) Provisional application No. 62/161,986, filed on May 15, 2015.

(51) Int. Cl.
*A61K 9/00* (2006.01)
*A61K 9/16* (2006.01)
*A61K 31/704* (2006.01)
*A61K 51/12* (2006.01)
*A61M 5/142* (2006.01)
*A61M 31/00* (2006.01)
*A61M 37/00* (2006.01)

(52) U.S. Cl.
CPC ............. *A61K 9/0024* (2013.01); *A61K 9/16* (2013.01); *A61K 31/704* (2013.01); *A61K 51/1282* (2013.01); *A61M 31/002* (2013.01); *A61M 31/005* (2013.01); *A61M 37/0069* (2013.01); *A61M 5/14276* (2013.01)

(58) Field of Classification Search
CPC ...... A61K 9/0024; A61K 9/16; A61K 31/704; A61K 51/1282; A61M 31/002; A61M 31/005; A61M 37/0069; A61M 5/14276
See application file for complete search history.

(56) References Cited

U.S. PATENT DOCUMENTS

| | | |
|---|---|---|
| 4,938,949 A | 7/1990 | Borch et al. |
| 2005/0031689 A1 | 2/2005 | Shults |
| 2010/0152699 A1 | 6/2010 | Ferrari et al. |
| 2012/0171292 A1 | 7/2012 | Sailor et al. |
| 2013/0131628 A1 | 5/2013 | Grattoni et al. |
| 2013/0211368 A1 | 8/2013 | Martin et al. |
| 2014/0342015 A1 | 11/2014 | Murphy |
| 2016/0324642 A1 | 11/2016 | Maria De Peppo |

FOREIGN PATENT DOCUMENTS

| | | |
|---|---|---|
| EP | 2597148 | 5/2013 |
| WO | 2010056986 | 5/2010 |
| WO | 2010105058 | 9/2010 |
| WO | 2010120817 | 10/2010 |
| WO | 2013112734 | 8/2013 |

OTHER PUBLICATIONS

Allard et al., Local delivery of ferrociphenol lipid nanocapsules followed by external radiotherapy as a synergistic treatment against intracranial 9L glioma xenograft. Pharm Res, 2010. 27(1): p. 56-64.
Ansari et al. Radiofrequency ablation or percutaneous ethanol injection for the treatment of liver tumors. World J Gastroenterol, 2012. 18(10): p. 1003-8.
Chonan et al. CD40/CD40L expression correlates with the survival of patients with glioblastomas and an augmentation in CD40 signaling enhances the efficacy of vaccinations against glioma models. Neuro Oncol. 2015, 17(11), 1453-62.
Cosentino et al. Dynamic Model of Bimolecular Diffusion through Two-Dimensional Nanochannels. J Phys Chem B 2005, 109, 7358-7364.
Diop-Frimpong et al. Losartan inhibits collagen I synthesis and improves the distribution and efficacy of nanotherapeutics in tumors. Proceedings of the National Academy of Sciences. 108, 2909-2914 (2011).
Dong, et al., Intratumoral delivery of beta-lapachone via polymer implants for prostate cancer therapy. Clin Cancer Res, 2009. 15(1): p. 131-9.
Dubrot et al., Intratumoral injection of interferon-alpha and systemic delivery of agonist anti-CD137 monoclonal antibodies synergize for immunotherapy. Int J Cancer, 2011. 128(1): p. 105-18.
Ferrati et al. Delivering enhanced testosterone replacement therapy through nanochannels. The journal of sexual medicine. 2015, 4(3), 446-251.
Ferrati et al. The nanochannel delivery system for constant testosterone replacement therapy. The journal of sexual medicine. 2015, 12(6), 1375-1380.
Ferrati et al., Leveraging nanochannels for universal, zero-order drug delivery in vivo. J Control Release, 2013. 172(3): p. 1011-9.
Fine et al. Silicon Micro- and Nanofabrication for Medicine. Advanced healthcare materials. 2013, 2, 632-666.
Fine et al., A robust nanofluidic membrane with tunable zero-order release for implantable dose specific drug delivery. Lab Chip, 2010. 10(22): p. 3074-83.

(Continued)

*Primary Examiner* — Robert A Wax
*Assistant Examiner* — Quanglong N Truong
(74) *Attorney, Agent, or Firm* — Womble Bond Dickinson (US) LLP

(57) ABSTRACT

An implantable device comprising a nanochanneled membrane is described. The device uses nanofluidics to control the delivery of diagnostic and/or therapeutic agents intratumorally. The devices can be used for chemotherapy, radiosensitization, immunomodulation, and imaging contrast.

15 Claims, 13 Drawing Sheets

(56) References Cited

OTHER PUBLICATIONS

Fuso Nerini et al. Instratumor heterogeneity and its impact on drug distribution and sensitivity. Clinical Pharmacology & Therapeutics. 96, 224-238 (2014).
Gerloni et al. Functional cooperation between T helper cell determinants. Proc Natl Acad Sci U S A. 97, 13269-74 (2000).
Goldberg et al., Intratumoral cancer chemotherapy and immunotherapy: opportunities for nonsystemic preoperative drug delivery. Journal of Pharmacy and Pharmacology, 2002. 54(2): p. 159-180.
Grattoni et al. Gated and near-surface diffusion of charged fullerenes in nanochannels. ACS nano. 5, 9382-9391 (2011).
Grattoni et al. Device for Rapid and Agile Measurement of Diffusivity in Micro- and Nanochannels. Anal Chem. 83, 3096-103 (2011).
Grattoni et al., Nanochannel technology for constant delivery of chemotherapeutics: beyond metronomic administration. Pharm Res, 2011. 28(2): p. 292-300.
Guerin et al., Recent advances in brain tumor therapy: local intracerebral drug delivery by polymers. Invest New Drugs, 2004. 22(1): p. 27-37.
Guo et al., Enhanced 4T1 breast carcinoma anticancer activity by co-delivery of doxorubicin and curcumin with core-shell drug-carrier based on heparin modified poly(L-lactide) grafted polyethylenimine cationic nanoparticles. J Biomed Nanotechnol, 2014. 10(2): p. 227-37.
Hekmat et al. The effects of silver nanoparticles and doxorubicin combination on DNA structure and its antiproliferative effect against T47D and MCF7 cell lines. Journal of biomedical nanotechnology. 8, 968-982 (2012).
Holohan et al., Cancer drug resistance: an evolving paradigm. Nature Reviews Cancer, 2013. 13(10): p. 714-726.
Hood et al., Fiberoptic microneedle device facilitates volumetric infusate dispersion during convection-enhanced delivery in the brain. Lasers Surg Med, 2013. 45(7): p. 418-26.
Kalyanaraman et al. Doxorubicin-induced apoptosis: Implications in cariotoxicity. Oxygen/Nitrogen Radicals: Cell Injury and Disease, Springer, 2002, pp. 119-214.
Kaufman et al. Local delivery of vaccinia virus expressing multiple costimulatory molecules for the treatment of established tumors. Hum Gene Ther, 2006. 17(2): p. 239-44.
Lesinski et al., Release of biologically functional interferon-alpha from a nanochannel delivery system. Biomed Microdevices, 2005. 7(1): p. 71-9.
Lesniak et al. Local delivery of doxorubicin for the treatment of malignant brain tumors in rats. Anticancer research. 25, 3825-3831 (2005).
Marabelle et al. Depleting tumor-secific Tregs at a signle site eradicates disseminated tumors. The Journal of clinical investigation. 123, 2447 (2013).
Marabelle et al., Intratumoral immunization: a new paradigm for cancer therapy. Clin Cancer Res, 2014. 20(7): p. 1747-56.
Martin et al. Tailoring width of microfabricated nanochannels to solute size can be used to control diffusion kinetics. J Control Release 2005; 102(1); 123-33.
Milo et al. BioNumbers—the database of key numbers in molecular and cell biology. Nucleic acids research. 38, D750-D753 (2010).
Mitra et al. Tumour targeted delivery of encapsulated dextran-doxorubicin conjugate using chitosan nanoparticles as carrier. Journal of Controlled Release. 74, 317-323 (2001).
Orlowski et al. Randomized phase III study of pegylated liposomal doxorubicin plus bortezeomib compared with bortezomib alone in relapsed or refractory multiple myeloma: combination therepy improves time to progression. Journal of Clinical Oncology. 25, 3892-3901 (2007).
Panchuk et al., Application of C-60 Fullerene-Doxorubicin Complex for Tumor Cell Treatment In Vitro and In Vivo. Journal of Biomedical Nanotechnology, 2015. 11(7): p. 1139-1152.
Patel et al. Low dose rate vs. High dose rate brachytherapy in the treatment of carcinoma of the uterine cervix: A clinical trial. International Journal of Radiation Oncology* Biology* Physics. 1994, 28, 335-341.
Piconese et al. OX40 triggering blocks suppression by regulatory T cells and facilitates tumor rejection. J Exp Med. 205, 825-39 (2008).
Rebucci et al. Molecular aspects of cancer cell resistance to chemotherapy. Biochemical pharmacology, 2013. 85(9): p. 1219-1226.
Sharma et al. Controlled-release microchips. Expert Opin Drug Deliv 2006: 3(3): 379-94.
Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17.
Walczak et al. Long-term biocompatibility of NanoGATE drug delivery implant. Nanobiotechnology, 2005, 1, 35-42.
Weinberg et al. Polymer implants for intratumoral drug delivery and cancer therapy. J Pharm Sci, 2008. 97(5): p. 1681-702.
Yapp et al., The potentiation of the effect of radiation treatment by intratumoral delivery of cisplatin. Int J Radiat Oncol Biol Phys, 1998. 42(2): p. 413-20.
Ziemys et al. Hierarchical modeling of diffusive transport through nanochannels by coupling molecular dynamics with finite element method. Journal of Computational Physics. 2011, 230(14), 5722-5731.
International Search Report and Written Opinion issued Aug. 16, 2016 in International Application PCT/US2016/032658 (8 pages).

Contents of nDS Implant from Sprague-Dawley rats

| | |
|---|---|
| Serum albumin | Actin cytoplasmic 1 |
| Alpha 2 HS glycoprotein | Actin cytoplasmic 2 |
| Serine protease inhibitor A3K | Apolipoprotein A I |
| Hemoglobin subunit beta 1 | T kininogen 2 |
| Serine protease inhibitor A3L | Alcohol dehydrogenase 1 |
| Alpha 1 inhibitor 3 | Ig lambda 2 chain C region |
| Serotransferrin | Fibronectin |
| Hemopexin | Ig gamma 1 chain C region |
| Ig kappa chain C region A | Plasminogen |
| Serine protease inhibitor 2 1 Fragment | Apolipoprotein A IV |
| Hemoglobin subunit alpha 1 2 | Actin alpha skeletal muscle |
| Murinoglobulin 1 | Histone H2A type 1 |
| Vitamin D binding protein | Cystatin C |
| Hemoglobin subunit beta 2 | Gelsolin |
| Murinoglobulin 2 | Fibrinogen gamma chain |
| Alpha 1 antiproteinase | Beta 2 glycoprotein 1 |
| Fetuin B | Fibrinogen beta chain |
| Apolipoprotein E | Carboxylesterase 1C |
| Complement C3 | Complement C4 |
| Serine protease inhibitor A3N | Histidine rich glycoprotein |
| Alpha 1 macroglobulin | C reactive protein |
| Ig gamma 2A chain C region | Collagen alpha 1 I chain |
| Serine protease inhibitor A3M Fragment | Fibrinogen alpha chain |
| Ig gamma 2B chain C region | Ig gamma 2C chain C region |
| Afamin | Inter alpha trypsin inhibitor heavy chain H3 |
| Haptoglobin | Complement factor I |
| T kininogen 1 | Ceruloplasmin |
| Protein AMBP | Kininogen 1 |

FIG.3C

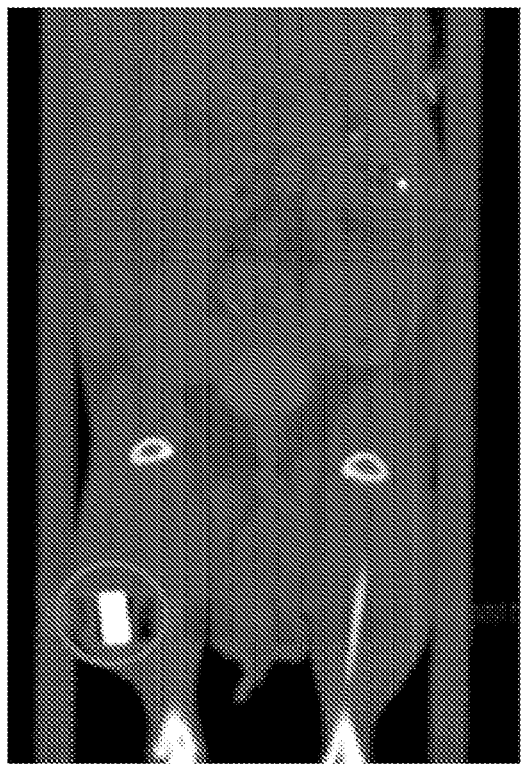
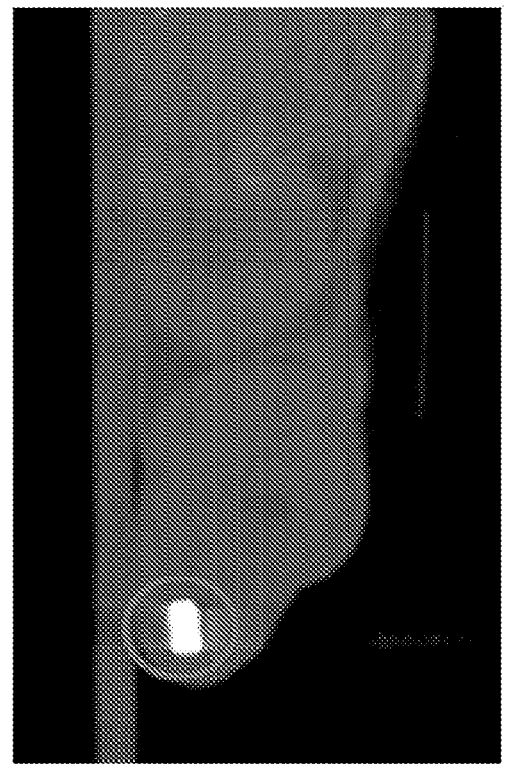
FIG.9A  FIG.9B
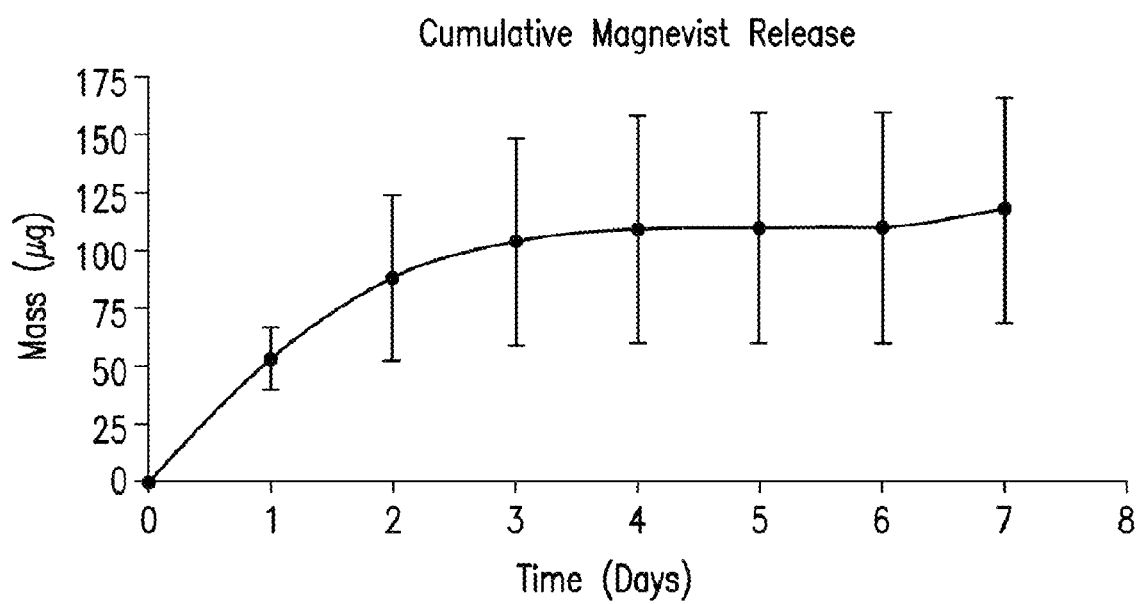
FIG.10

IMPLANTABLE NANOCHANNEL DELIVERY DEVICES

CROSS-REFERENCE TO RELATED APPLICATIONS

This application is a continuation of U.S. patent application Ser. No. 16/879,984, filed May 21, 2020, which is a continuation of U.S. patent application Ser. No. 15/574,185, filed Nov. 15, 2017, which is a 371 U.S. National Stage of International Application No. PCT/US2016/032658, filed May 16, 2016, which claims the benefit of U.S. Provisional Application No. 62/161,986, filed May 15, 2015, each of which is hereby incorporated herein by reference in their entireties for all purposes.

BACKGROUND

Conventional standard-of-care for most oncological interventions entails surgical resection followed by radiation and systemic chemotherapy. This approach has remained the clinical mainstay despite recognition of the toxicity typical of systemic chemotherapy and immunotherapy that frequently limits treatment efficacy and reduces quality of life for many patients (Panchuk, et al., *J Biomed Nanotech.* 11, 1139-1152 (2015); G. B. Lesinski, et al., *Biomed Microdevices.* 7, 71-9 (2005); E. P. Goldberg, et al., *J Pharmacy Pharmacol.* 54, 159-180 (2002)). This is in addition to known drawbacks such as insufficient local concentration of chemotherapeutics that induce drug resistance within tumor cell populations (C. Holohan, et al., *Nature Rev Cancer.* 13, 714-726 (2013); M. Rebucci, et al., *Biochemical Pharmacol.* 85, 1219-1226 (2013)). These weaknesses have motivated development of local, intratumoral administration methods that have been demonstrated to require substantially reduced overall dosages of drug, lowering systemic toxicity while increasing intratumoral drug concentrations (D. T. Yapp, et al., *Int J Radiat Oncol Biol Phys.* 42, 413-20 (1998); A. Marabelle, et al., *Clin Cancer Res.* 20, 1747-56 (2014)). Several approaches to intratumoral delivery of chemo- and immunotherapy have been developed, including direct infusion (J. Dubrot, et al., *Int J Cancer.* 128, 105-18 (2011); D. Ansari, et al., *World J Gastroenterol.* 18, 1003-8 (2012); R. L. Hood, et al., *Lasers Surg Med.* 45, 418-26 (2013); H. L. Kaufman, et al., *Human Gene Therapy.* 17, 239-244 (2006)), biodegradable polymers (C. Guerin, et al., *Invest New Drugs.* 22, 27-37 (2004); Y. Dong, et al., *Clin Cancer Res.* 15, 131-9 (2009); B. D. Weinberg, et al., *J Pharm Sci.* 97, 1681-702 (2008)), and nanoparticle conjugation (E. Allard, et al., *Pharm Res.* 27, 56-64 (2010); O. Guo, et al., *J Biomed Nanotechnol.* 10, 227-37 (2014)). Apparent drawbacks to these approaches include rapid metabolism and clearance, burst release kinetics with a rapid peak followed by a trough, and reliance on materials that are unlikely to be approved by the FDA, respectively. What is thus needed is a bioinert platform that provides persistent intratumoral release over several days. The compositions and methods disclosed herein address this and other needs.

SUMMARY

In accordance with the purposes of the disclosed materials, compounds, compositions, articles, and methods, as embodied and broadly described herein, the disclosed subject matter relates to compositions, methods of making said compositions, and methods of using said compositions. More specifically, disclosed herein is an implantable fiducial marker or radioactive seed for image guided radiotherapy or local radiotherapy, respectively, which hosts a drug and/or particle contained within a reservoir and a nanochannel membrane for the simultaneous and controlled local administration of therapeutics for oncology applications (FIG. 1). The reservoir can host molecules (drugs), particles, and/or large biologics in liquid, solid powder, emulsions, gel or solid degradable formulations. The reservoir can be composed of a cap or a septum through which the particles and/or drug is inserted. The fiducial marker or seed has the nanochannel membrane at one end. The nanochannel membrane can be fabricated through photolithographic techniques with nanochannel tight dimensional tolerances, allowing the controlled, constant administration of drugs or particles for sustained periods of time to be given in concert to radiation delivered via image guide radiotherapy or radioactive seeds.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

FIG. 2A is a photograph of the capsule. FIG. 2B and FIG. 2C are SEMs of the implant. FIG. 2D is a TEM of nanochannel membrane sectioned by focused ion beam. Note the capsules are assemble with the macrochannel side of the membrane facing outward to protect the nanochannels. The silicone rubber septa for drug loading and fluid retrieval, the nanochannel membrane, the radiopaque drug reservoir and the epoxy sealant are also shown.

FIG. 3C is a table of exemplary compositions that can be used in the disclosed devices.

Error bars show one standard deviation between replicates. $R^2$ for biphasic linear regressions are 0.88, 0.96 for OX86 and 0.99, 0.96 for FGK45.

Figure 8:
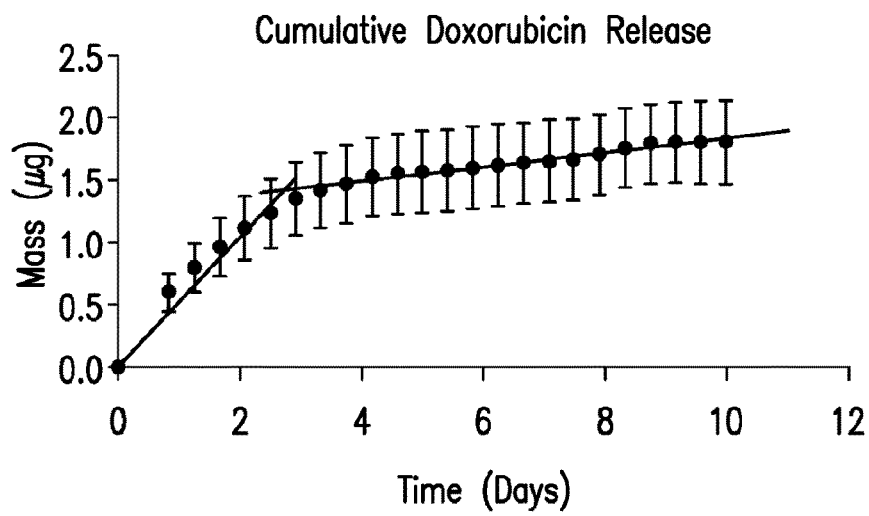

FIG. 8 is a graph that shows the mean cumulative release of doxorubicin (n=5) from the nanochannel implants in vitro. This graph includes data sampled 1 out of every 60 points recorded. Error bars show one standard deviation between replicates. $R^2$ for the biphasic linear regression is 0.93, 0.97.

FIG. 9A is a coronal, and FIG. 9B is a sagittal, plane CT image of a stainless steel nanochannel implant. Implants exhibited high imaging contrast and demonstrated their capability as a radiofiducial.

Figure 11A:
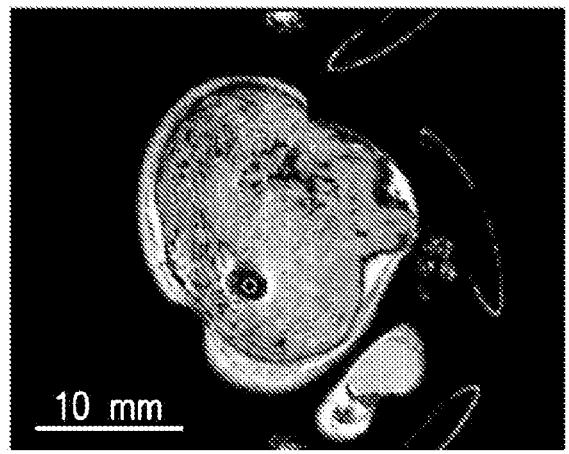
Figure 11B:
Figure 11C:
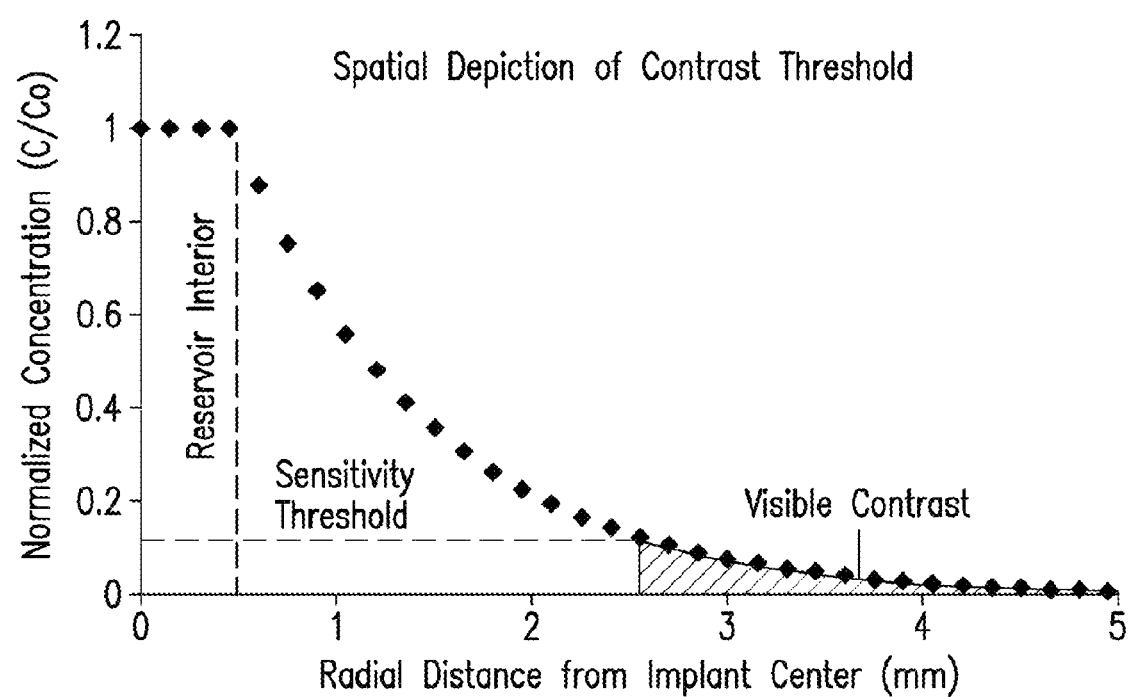

FIG. 10 is a graph of cumulative release of Magnevist (n=4) from nanochannel implants in vitro. Error bars show one standard deviation between replicates. $R^2$ for biphasic linear regressions are 0.98, 0.83:

FIG. 11A and FIG. 11B are MR images from a representative mouse. FIG. 11A is a T1-weighted image, and FIG. 11B is a T2-weighted image. The rings depict the estimated implant location. FIG. 11C provides a depiction of the visible contrast threshold as concentration diminishes exponentially as Magnevist diffuses away from the implant reservoir. Unmeasurably quick signal response time rendered volumes with high Magnevist concentration as voids.

Figure 12A:
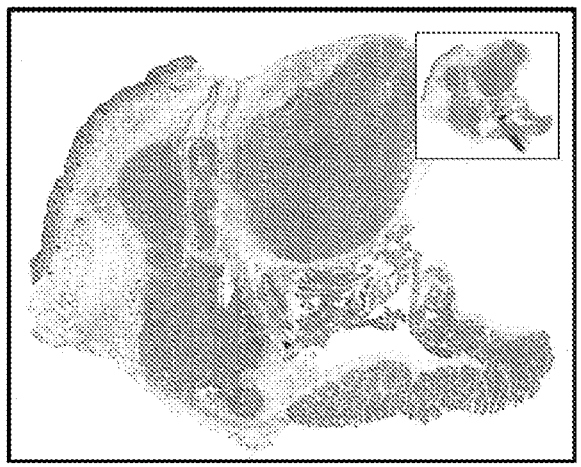
Figure 12B:
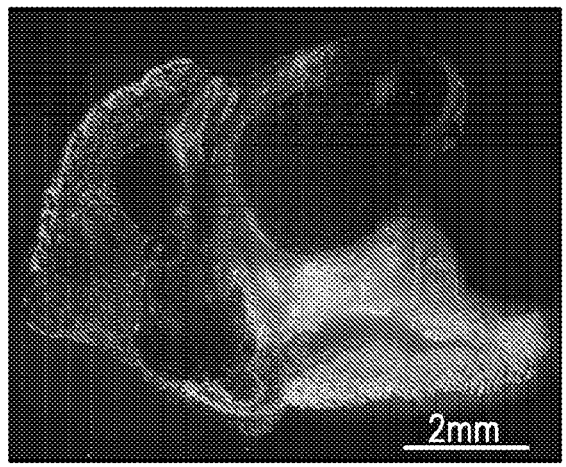

FIG. 12A and FIG. 12B are images of an excised subcutaneous PANC-1 tumor mass implanted with a locally implanted nanochannel device releasing IgG conjugated with Alexa Fluor 488. FIG. 12A is a brightfield image of the H&E stained tissue and, FIG. 12B is a FITC-filtered fluorescent image exhibiting the diffusing released analytes. Inset exhibits the approximate location and orientation of the device relative to the plane of the section.

Figure 13:
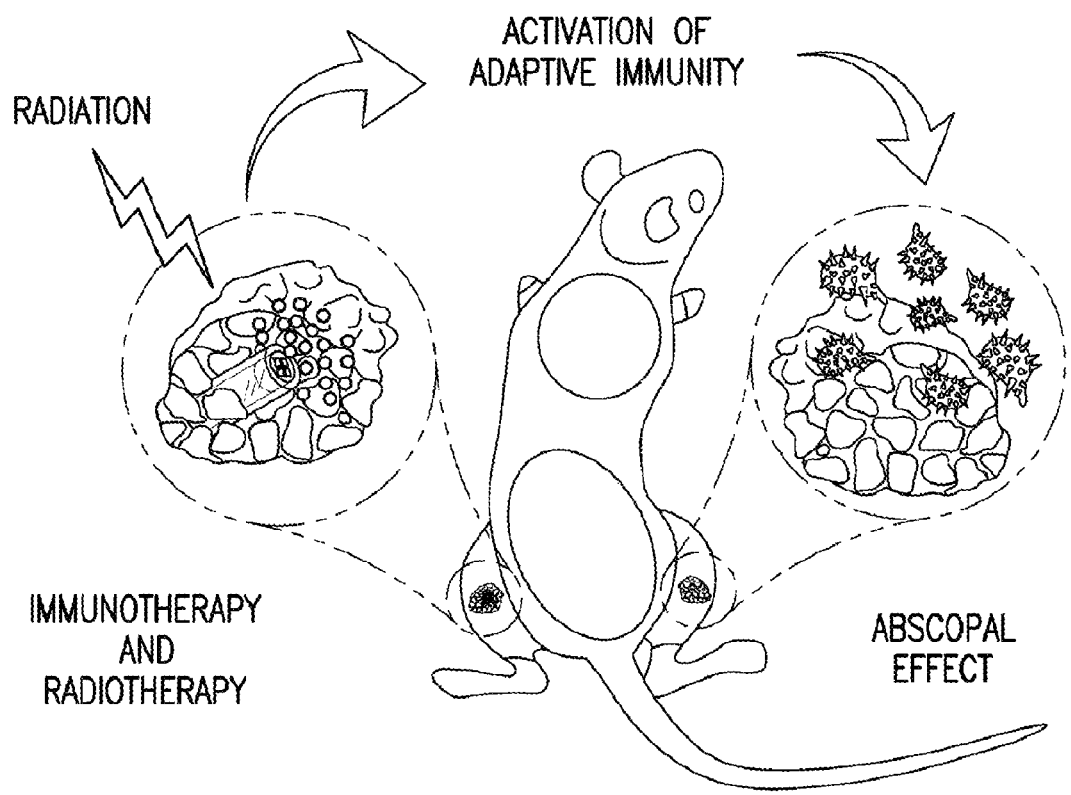

FIG. 13 is a schematic showing the treatment strategy for nDSmini immunotherapy together with radiotherapy in a bilateral tumor model.

Figure 14A:
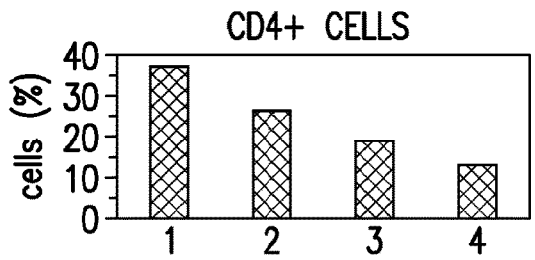
Figure 14B:
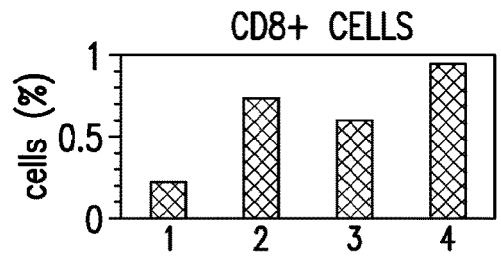

FIG. 14A and FIG. 14B are graphs showing splenocyte population analysis through FACS for each group in Table 3.

Figure 15A:
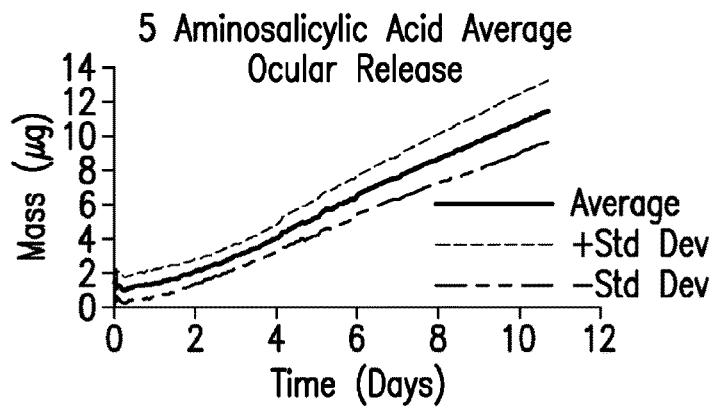
Figure 15B:
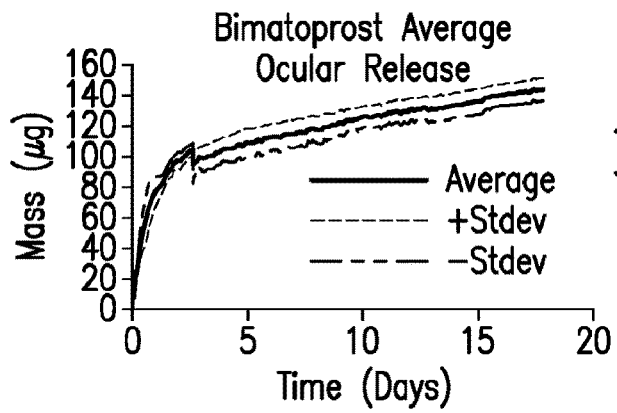
Figure 15C:
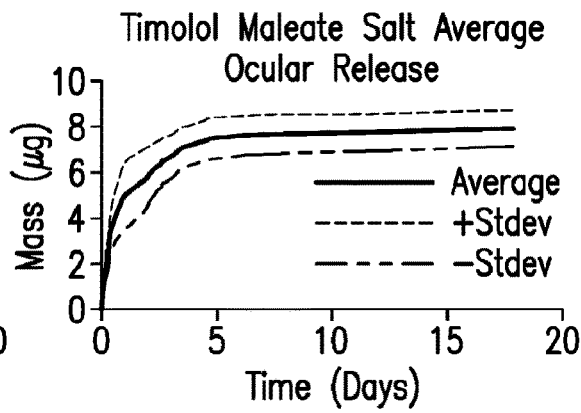

FIG. 15A, FIG. 15B, and FIG. 15C are graphs of the average cumulative release of 5-aminosalicylic acid (FIG. 15A), bimatoprost (FIG. 15B), and timolol maleate (FIG. 15C) from the ocular nDSmini. The experiment was conducted at n=3, 5, and 5 for A, B, and C, respectively.

Figure 16A:
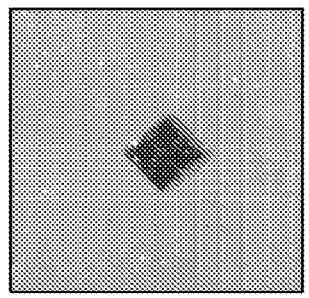
Figure 16B:
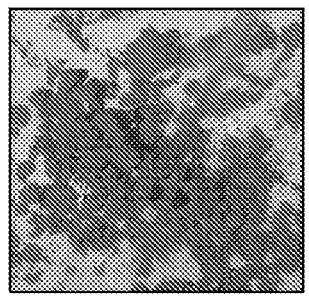
Figure 16C:
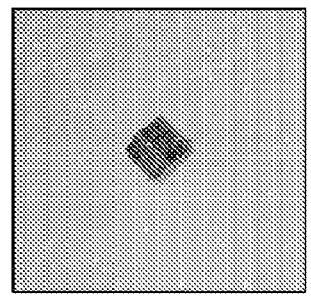

FIG. 16A, FIG. 16B, and FIG. 16C are pictures showing a powder loading sequence. FIG. 16A is an unfilled 2×2 diced silicon membrane, macrochannel side; FIG. 16B is a Rhodamine B powder packing; and FIG. 16C is the packed membrane.

Figure 17A:
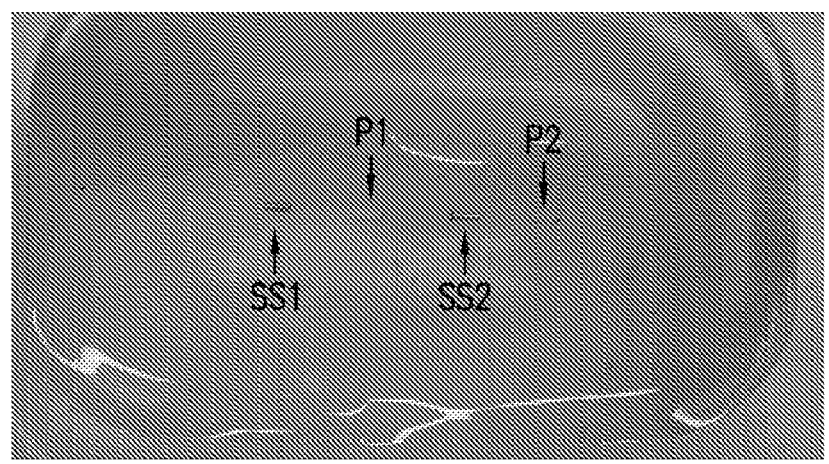
Figure 17B:
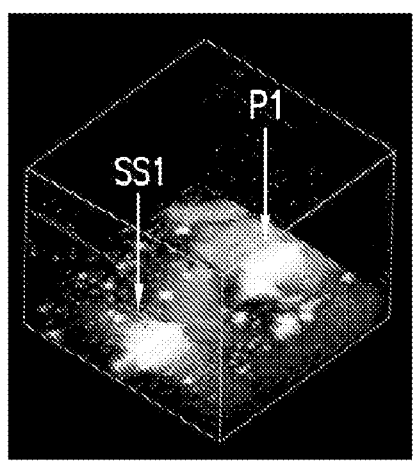
Figure 17C:
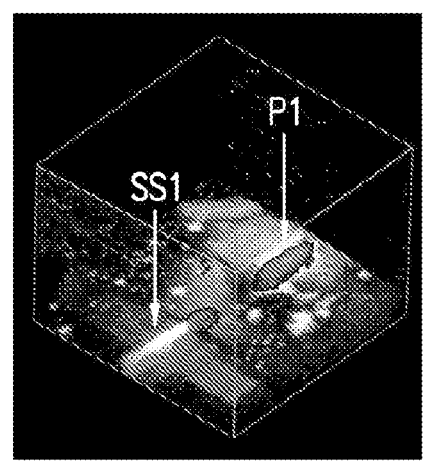

FIG. 17A shows four nDSminis in a transparent gelatin tissue phantom, two SS and two P. FIG. 17B shows US Bmode image of SS and P nDSminis. FIG. 17C shows PA scan (red) superimposed over US (grey) of same nDSminis.

Figure 18A:
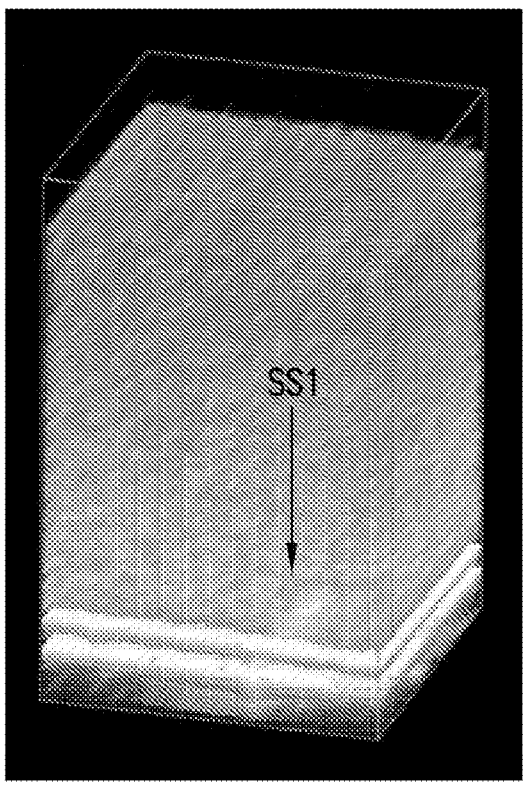
Figure 18B:
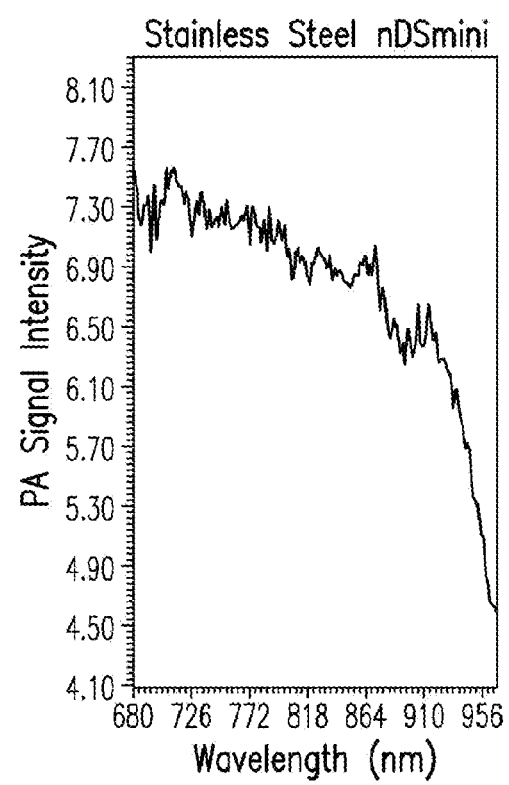

FIG. 18A shows SS nDSmini embedded 1.4 cm into tissue mimicking phantom. The US Bmode image (grey) with overlaid PA image (red). FIG. 18B shows the spectral response of SS nDSmini to PA scan.

Figure 19A:
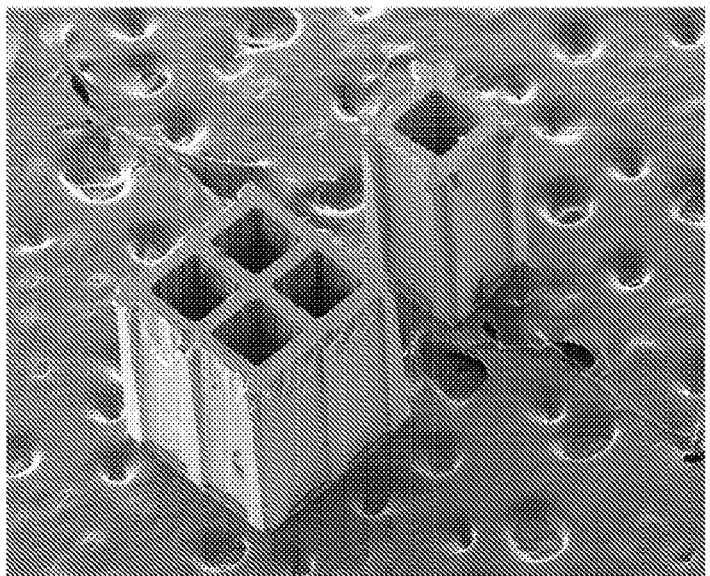
Figure 19B:
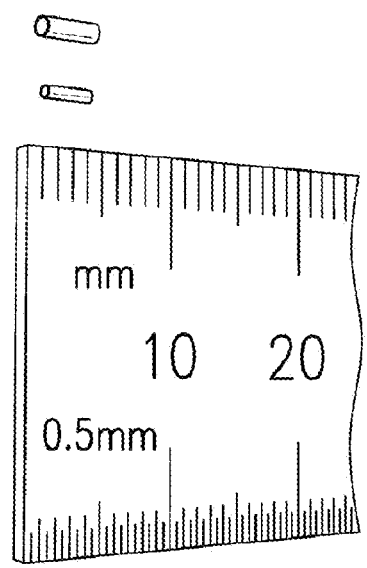

FIG. 19A is a SEM of the 2×2 and 1×1 diced silicon membrane variants. FIG. 19B is a fabricated nDSmini device mounting the 2×2 and 1×1 membranes.

DETAILED DESCRIPTION

The materials, compounds, compositions, and methods described herein may be understood more readily by reference to the following detailed description of specific aspects of the disclosed subject matter and the Figures and Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

Fiducial Markers, Capsules, and Seeds

Disclosed herein is an implantable device (a fiducial marker, capsule or seed) comprising a membrane that offers tightly-controlled release of drugs, particles, and/or biomolecules through its high spatial and electrostatic hindrance within 100,000s of parallel nanochannels. Relying on concentration-driven diffusive transport, these nanochanneled membranes provide a drug agnostic delivery mechanism. By integrating this technology within a small implantable device designed for application, the implant can offer multipurpose functionality to work synergistically with different therapeutic approaches and clinical imaging systems. These small implants permit serial implantation throughout a tissue volume via a minimally-invasive, percutaneous trocar delivery mechanism. Experiments demonstrate that this platform is capable of delivering chemotherapy, radiosensitization, immunomodulation, immunotherapy, and imaging contrast, among others. The broad versatility of this system is demonstrated herein through a series of different experiments exhibiting clinically-relevant dosage release of doxorubicin, OX86, FGK45, and Magnevist. Further experiments demonstrated successful implantation and intratumoral release, as well as the platform's capability to serve as a radiofiducial. These results provide strong evidence of a flexible, multifunctional nanofluidic implant capable of substantially broadening local delivery utility in the clinic. There are also the likely benefits of avoidance of drug/dose limiting systemic toxicity. This is attractive because of the toxicity of systemic therapy (pancytopenia, nausea, vomiting etc.) is so great and often dictates treatment allocation. The disclosed devices were also well-tolerated without abnormal wound healing or adverse immune reactions being observed.

Nanochanneled Membrane

Nanochanneled membranes for long term controlled release of drugs from implantable devices are described in, e.g., Sharma et al., *Expert Opin Drug Deliv.* 3(3):379-94 (2006) and Martin et al., "Tailoring width of microfabricated nanochannels to solute size can be used to control diffusion kinetics," *J. Control Release* 102(1):123-33 (2005). Methods for the fabrication of silicon-based mechanically robust devices with hundreds of thousands of densely packed nanochannels with precisely controlled size and surface properties is described in Grattoni et al., "A robust nanofluidic membrane with tunable zero-order release for implantable dose specific drug delivery," *Lab on a Chip* 10:3074-3083 (2010). Sacrificial layer techniques have been used to reproducibly fabricate nanochannels as small as 3 nm. The nanoscale fluidics have been analyzed and new predictive laws for molecular diffusion in nanochannels have been developed and demonstrated (Cosentino et al., "Dynamic Model of Biomolecular Diffusion through Two-Dimensional Nanochannels," *J Phys. Chem. B* 109:7358-7364 (2005); Ziemys et al., "Hierarchical modeling of diffusive transport through nanochannels by coupling molecular dynamics with finite element method," *J Computational Physics.* (2010)). At the nanoscale, molecular interactions with the channel wall dominate the transport of fluids to such an extent that the classical mechanical laws of diffusion (Fick's laws) break down. Thus, nanoscale phenomena are used herein to achieve the goal of constant release of nanoparticles and therapeutics over periods of time ranging from weeks to months and over a broad range of molecular sizes, at release rates relevant for medical applications (Grattoni et al., "A robust nanofluidic membrane with tunable zero-order release for implantable dose specific drug delivery," *Lab on a Chip* 10:3074-3083 (2010)). Constant and sustained release was achieved with a large number of molecules ranging from small molecular weight (MW) peptides such as leuprolide (Grattoni et al., "Nanochannel Technology for Metronomic Delivery of Chemotherapeutics," *Pharm. Res.* 28(2):292-300 (2011)), a LH-RH agonist and common treatment for prostatic cancer, as well as large MW proteins such as bevacizumab, a monoclonal antibody to VEGF widely used in the treatment of metastatic colon cancer and other diseases. It has also been demonstrated, both in vitro and in vivo, the constant delivery of Interferon a-2b and lysozyme in a healthy rat model for over 6 months (Walczak et al., "Long-term biocompatibility of NanoGATE drug delivery implant," *Nanobiotechnology* 1:35-42 (2005)). The experimental analysis has been focused on the release of drug from solutions stored in a source reservoir.

The nanochannels can be fabricated with varying height and channel density, enabling tuning to fit a given molecule and desired dose release rate. For example, the nanochanneled membranes can have nanochannels from 2.5 nm to 100 nm in diameter, for example, from 2.5 nm to 75 nm, from 2.5 nm to 50 nm, from 2.5 to 25 nm, from 5 nm to 75 nm, from 5 nm to 50 nm, from 5 nm to 25 nm, from 10 nm to 75 nm, from 10 nm to 50 nm, from 10 nm to 25 nm, from 20 nm to 75 nm, from 20 nm to 50 nm, from 40 nm to 100 nm, from 40 nm to 75 nm, from 50 nm to 100 nm, from 50 nm to 75 nm, from or from 75 nm to 100 nm. The density of the nanochannels in the membrane can be at least 50,000, 100,000, or 150,000 nanochannels mm$^{-2}$.

As the nanochannel membranes themselves can be mass produced using well-understood fabrication techniques refined by the semiconductor industry and the other components are low cost.

Tubular Body

The devices disclosed herein have a tubular body. The body can be made of a material that is biologically acceptable, e.g., does not illicit an immune response. The body can be biodegradable or non-biodegradable. In certain aspects, the body can be made of titanium, tungsten, gold, or stainless steel.

The size of the tubular body can be varied depending on the contents of the reservoir, the volume of the reservoir, the intended use, and the like. Generally, the devices should be small enough to be injected through a syringe or cannula to the tumor. In some examples, the tubular body can have a length of less than 5 mm, e.g., less than 4, 3, 2, or 1 mm. For example, the tubular body can have a length of from 0.5 mm to 5 mm, from 1 mm to 5 mm, from 1 mm to 3 mm, from 1 mm to 2 mm, or from 0.5 mm to 2 mm. In other examples, the tubular body can have a diameter of less than 2 mm, e.g., less than 1 mm, 0.9 mm, 0.8 mm, 0.7 mm, 0.6 mm, 0.5 mm, 0.4 mm, 0.3 mm, 0.2 mm, or 0.1 mm. For example, the tubular body can have a diameter of from 0.1 mm to 2 mm, from 0.5 mm to 1 mm, from 1 to 2 mm, or from 0.1 to 0.5 mm.

Figure 1:
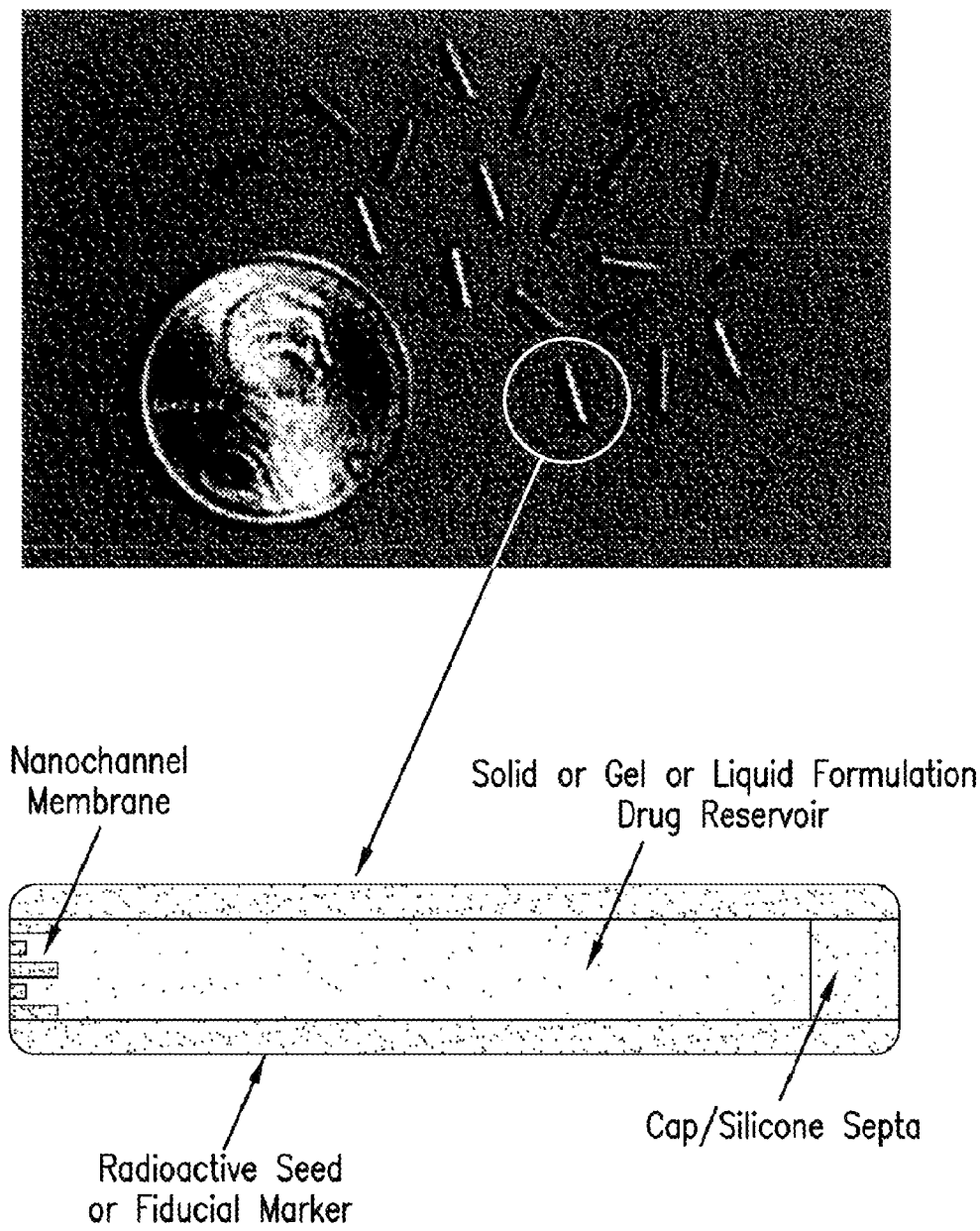
FIG. 1 is a photograph of a Fiducial Marker or Radioactive Therapeutic Delivery Seed, which is expanded to a longitudinal cross sectional view.
Figure 2A:
FIGS. 2A through 2D contain images of an assembled nanochannel implant.
Figure 2B:
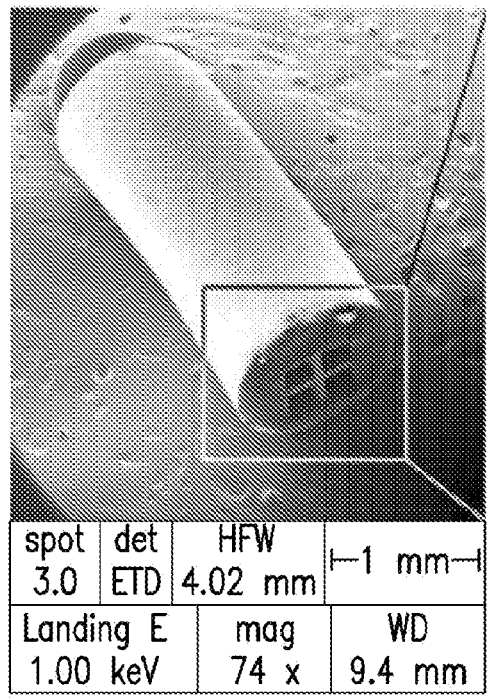
Figure 2C:
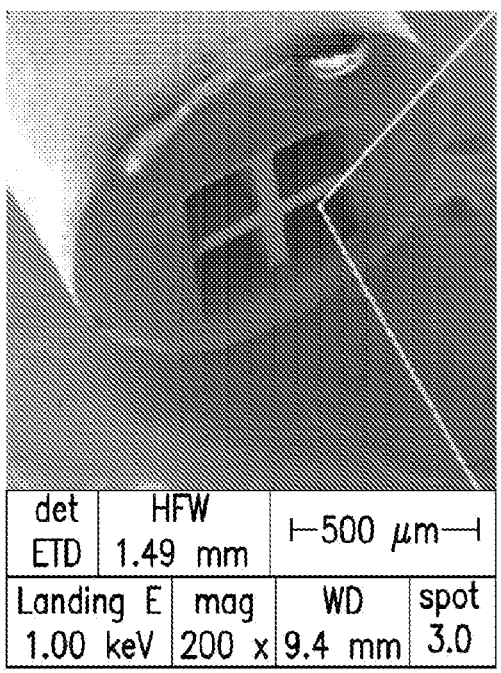
Figure 2D:
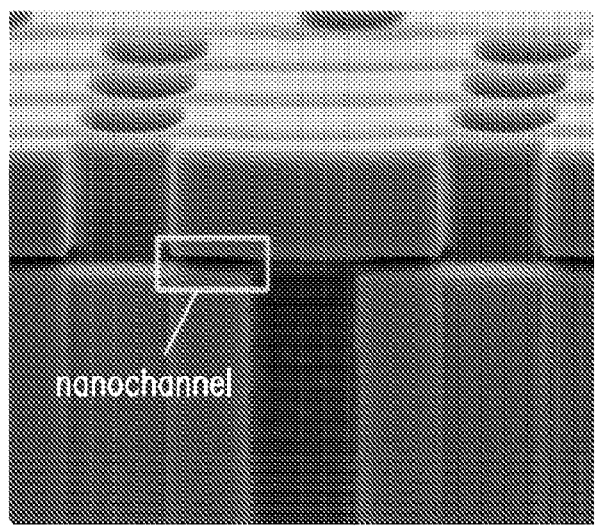

Examples of the devices disclosed herein have been prepared (see FIG. 1) and tested for molecular release. The device presented a length of 3.8 mm, a diameter of 1.1 mm and a drug reservoir volume of approximately 3 µL. The size of the implant was tailored to ease the insertion in to tumor mass (in rodents) by injection through a syringe. The 3.8 mm length was established to fit into a tumor mass in mice testing. Although there are no strict requirements for the device dimensions, the device can be ultimately tailored to match the size of commercially available fiducial markers and/or radioactive seeds. This would permit the use of insertion needles and deployment systems already adopted in the clinics.

The tubular body comprises a first end, which disposed therein is the nanochanneled membrane. The tubular body can also comprise a second end that can be an opening sealed with a plastic, rubber, or silicone. The payload can be filled into the reservoir through the second opening and then sealed.

Reservoir

Figure 3A:
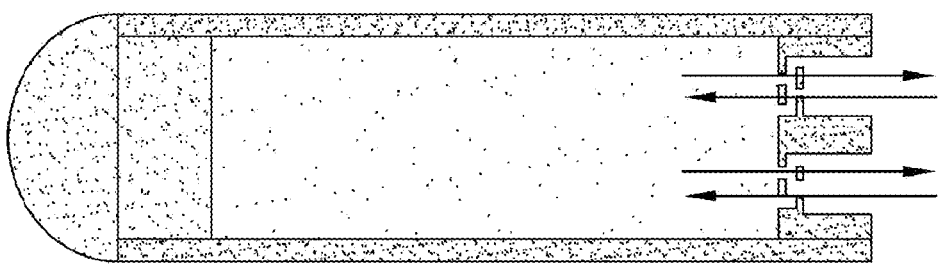
FIG. 3A contains a schematic of the agent release and molecule collection from and into the device.
Figure 3B:
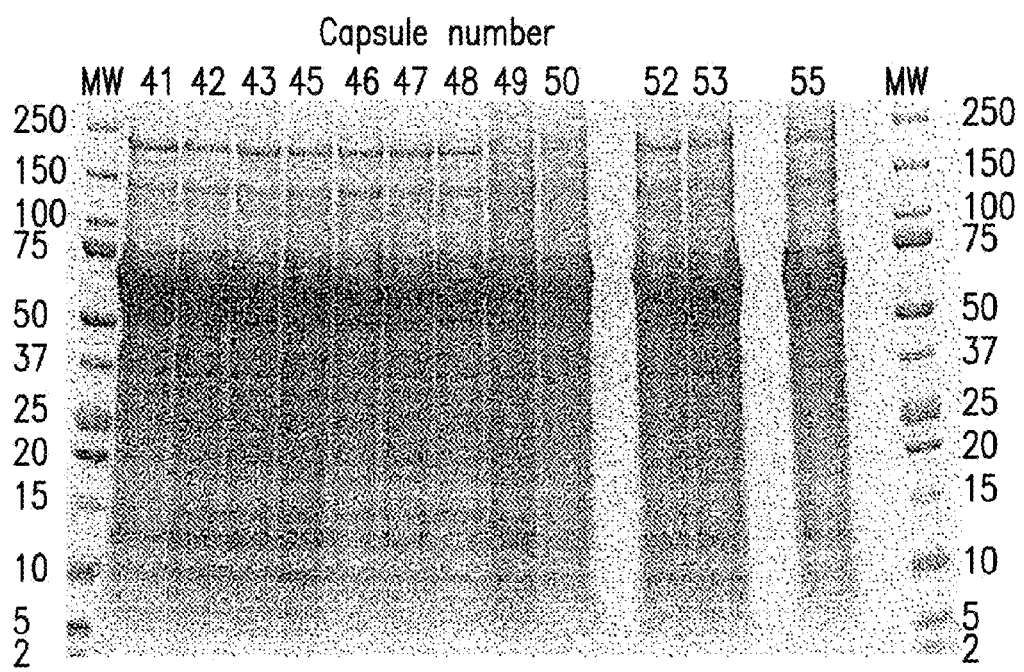
FIG. 3B shows total protein analysis on content of implants extracted from Sprague-Dawley rats after 60 days.

The reservoir of the disclosed devices can comprise a variety of compositions. As an example, the reservoir could be loaded with chemotherapeutics, antibodies, or viral nanoparticles, which, when locally injected, have shown to increase the efficacy of radiotherapy in prostate cancer treatment. The device can also be used to collect biological molecules from the site of insertion (e.g. tumor or organs) to allow for biomarker detection or discovery and fluid analysis (see FIG. 3C).

The reservoir can have volume of from 0.5 µL to 10 µL, for example, from 1 µL to 5 µL, from 2 µL to 6 µL, from 3 µL to 7 µL, from 4 µL to 9 µL, from 0.5 µL to 5 µL, from 1 µL to 5 µL, or from 5 µL to 10 µL. The small volume of each individual implant alleviates concerns of toxic reactions if an implant should be breached during implantation.

Payloads

The disclosed devices can be used to deliver various payloads within the reservoir. Radiosensitizers can be included within the reservoir. Examples of radiosensitizers that can be delivered by the disclosed devices include Topo1 inhibitors (paclitaxel, docetaxel, topotecan, camptothecin, irinotecan), PARP (poly ADP ribose polymerase) inhibitors (PARP1 and PARP2, most effective in BRCA1- or 2-deficient cells), HDAC (histone deacetylase) inhibitors (Vorinostat), HSP90 (heat shock protein) inhibitors (tanesipimycin), hypoxic cell cytotoxic agents (mitomycin-C, tirapazamine), membrane active agents (procaine, lidocaine, chlorpromazine), radiosensitizing nucleosides (5-fluorouracil, fluorodeoxyuridine, bromodeoxyuridine, lododeoxyuridine, hydroxyurea, gemcitabine, fludarabine), texaphyrins, suppressors of sulfhydral groups (N-ethylmalemide, diamide, diethylmaleate), general drugs (nicotinamide, metronidazole, curcumin), carbogen, nibrin (ATM inhibitor), nanoparticles (CaF, LaF, ZnS or ZnO quantum dots, gold, silver, superparamagnetic iron oxide nanoparticles from magnetite or magnemite, gadolinium, chitosan nanoparticles loaded with Gadolinium-157, hafnium oxide, titanium, aminosilanized oxidized silicon nanoparticles, $C_{60}$), NBTX-TOPO, Pt analogs (cisplatin, oxaliplatin), misonidzole, etanidazole, nimorazole, motexatin gadolinium (MGd), temozolomide, cetuximab (EGFR-targeted therapy), and farnesyl transferase inhibitors (FTI-277, L-744,832, and L-778,123).

In other examples, the reservoir can comprise $^{90}$Y, $^{177}$Lu, $^{18}$F, $^{64}$Cu, $^{67}$Cu, $^{89}$Zr, $^{124}$I, $^{123}$I, $^{152}$Eu, $^{99m}$Tc, $^{225}$Ac, $^{68}$Ga, or $^{111}$In. In other examples, the reservoir can comprise $^{192}$Ir.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, NJ) and HERCEPTIN (Genentech, Inc.; South San Francisco, CA), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., I131, I125, Y90, P32, etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

The reservoir can contain a payload with a dosage designed for a specific purpose. Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Methods

The devices disclosed herein can be a fiducial marker, gene/therapy delivery device, a radioisotope delivery device, and/or a chemotherapy device. In some examples, the disclosed devices can be used to facilitate in vivo imaging of and/or during cancer therapy. For example, image guided radiation therapy often times requires the placement of a fiducial marker to track tumor motion and gate the radiation beam to organ motion (movement of lung, liver lesions etc.). The device disclosed herein can be made of a material (e.g., titanium, tungsten, gold, stainless steel) which could be easily tracked radiographically. Further, data demonstrates a local synergistic effect and an anti-metastatic effect by treating locally with radiation in combination with a gene therapy agent (adv-HSV-tk). This combination can create a vaccine with the patient's own cancer cells. Thus the disclosed devices can be used as a fiducial marker and a gene therapy device.

The devices disclosed herein can be used as radioactive seeds. Radioactive seeds (brachytherapy) placed at the time of surgery can be used to treat malignancies. By having radioactive material in the reservoir, and/or the body made of radioactive material, they can be used in these therapies. Also, disclosed herein is a protocol where radioactive seeds and gene therapy are placed into patients with locally recurrent cancers, e.g., prostate cancer.

This same methodology could also be applied to other oncologic disease processes where in situ placement of seeds and therapeutic agent would increase cell kill and help initiate an immunological response. Often times these patients will require external beam radiation therapy after the placement of radioactive seeds. The disclosed devices can thus serves as a fiducial marker to help define and verify tumor location via image guidance (on board CT scanner that is on most radiation therapy machines). This would also allow imaging agent to be released during treatment to evaluate response to therapy (while receiving therapy).

It is also important to image the effect of treatment with the optimal contrast material or radiolabeled isotope. Thus, the disclosed devices can be used as an imaging agent.

The disclosed devices can also be used to deliver various chemotherapeutic agents (drugs and/or biologics). Current methods of drug administration are associated with peaks and troughs of drugs levels in the body. Such fluctuations effect drug efficacy and toxicities. The disclosed device removes much of these wide swings and hence can allow the administration of specific drugs (at lower overall amounts) with few side effects without compromising efficacy. Other advantages are that the devices do not require any movable components and therefore represents a stable system, which is less likely to suffer from damages as opposed to osmotic pumps and electromechanical systems. Also, the drug delivery devices can be used with radioactive seeds so the drugs/particles are controllably and locally administered in parallel with a radioactive therapy. So multiple injection of therapeutics are no longer needed. The radioactive seeds are commonly not retrieved after treatment is completed. By combining the drug delivery component into the radioactive seeds, there is no need to retrieve the drug delivery device at the end of its use.

The device can also be used to collect biological molecules from interstitial fluids from the implantation site (e.g. tumor, organs among others) for fluid analysis, marker detection or discovery, or tumor and tissue analysis. These collections can be without contaminants or cellular/tissue debris. Such sampling cannot currently be conducted by other means. Molecular collection form interstitial fluid has been demonstrated with a larger version of the implant inserted for 2 months subcutaneously in Sprague-Dawley rats. This process can be used to collect a molecular signature of tumors or tissues by automatically collecting a purified sample of interstitial fluids. The disclosed devices can allow for both the delivery of agents and the collection of molecules from the environment by simple inward diffusion.

The disclosed devices also can be used to evaluate tumor response during therapy by releasing imaging agents during the course of therapy. Thus by monitoring the imaging agent, on can determine the release of drug and its effect on the tumor.

In specific examples, provided herein are methods of treating or imaging cancer in a subject, comprising implanting into the subject a device as disclosed herein comprising an effective amount of an anticancer agent, radioactive agent, imaging agent, or gene therapy agent. The methods can further comprise implanting a second device as disclosed herein, compound or composition, such as, for example, anticancer agents or anti-inflammatory agents. Additionally, the method can further comprise administering an effective amount of ionizing radiation to the subject.

Methods of killing or imaging a tumor cell are also provided herein. The methods comprise contacting a tumor cell with a device as disclosed herein comprising an effective amount of an anticancer agent, radioactive agent, imaging agent, or gene therapy agent. The methods can further include administering a second compound or composition (e.g., an anticancer agent or an anti-inflammatory agent) and/or administering an effective amount of ionizing radiation to the subject.

Also provided herein are methods of radiotherapy of tumors, comprising implanting into a subject a device as disclosed herein comprising an effective amount of an anticancer agent, radioactive agent, imaging agent, or gene therapy agent, and delivering ionizing radiation to the tumor.

Also disclosed are methods for treating oncological disorders in a patient. In one embodiment, a device comprising an effective amount of one or more of an anticancer agent, radioactive agent, imaging agent, or gene therapy agent is implanted into a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Still other examples include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a device as disclosed herein comprising an effective amount of an anticancer agent, radioactive agent, imaging agent, or gene therapy agent and at least one cancer immunotherapeutic agent. The disclosed device can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, and anti-PDL1. Other immunotherapeutic agents include the TNFα antagonists (e.g. etanercept), the B cell depleting agent rituximab, the anti-IL-6 receptor tocilizumab, and the costimulation blocker abatacept can be administered with or in the disclosed devices.

The disclosed devices can also be administered with or contain toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed devices can also be administered with or contain an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

For the treatment of oncological disorders, the devices disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the devices disclosed herein. For example, the devices disclosed herein can be used in combination with or can themselves contain mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The devices disclosed herein can also be used alone or in combination with or can contain anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

EXAMPLES

Implantable Capsule Assembly

Nanochannels membranes were fabricated through industrial silicon manipulation processes initially developed within the microelectronics industry. The specifics of the disclosed process to produce nanochannel membranes have been described previously (e.g., A. Grattoni, et al., *Anal Chem.* 83, 3096-103 (2011)). Briefly, nanochannels with a height of 20 nm were generated within the silicon membranes through removal of atomic layer deposited tungsten (a sacrificial layer) by $H_2O_2$ etching. The resulting slit-nanochannels were characterized as having a defined and repeatable architecture. Individual channels were parallel to the membrane surface and perpendicular to microchannels running to either membrane surface. This configuration was adopted to promote high nanochannel density and physical robustness, as the membranes could withstand differential pressures in excess of 4 MPa (D. Fine, A. et al., *Adv Healthcare Mater.* 2, 632-666 (2013)). Following the sacrificial etching process, isopropyl alcohol was substituted for water prior to drying to minimize surface tension.

Figure 4A:
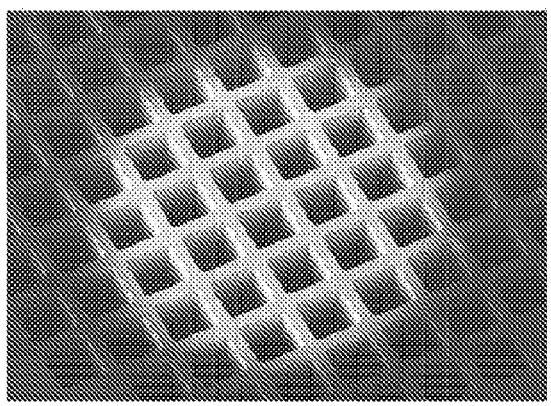
FIG. 4A and FIG. 4B are scanning electron microscope (SEM) images showing the macrochannel inlets of a nanochannel membrane before (FIG. 4A) and after (FIG. 4B) dicing with a precision dicing saw.
Figure 4B:
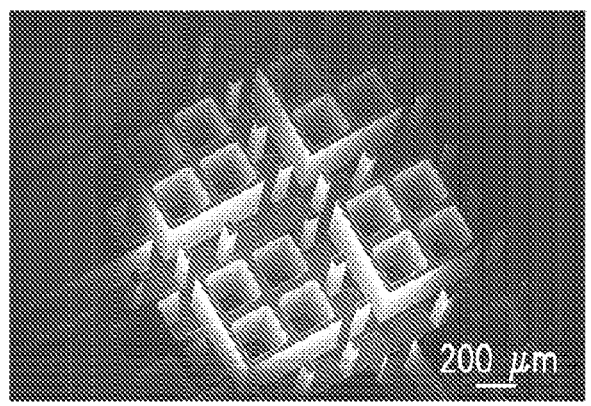
Figure 5:
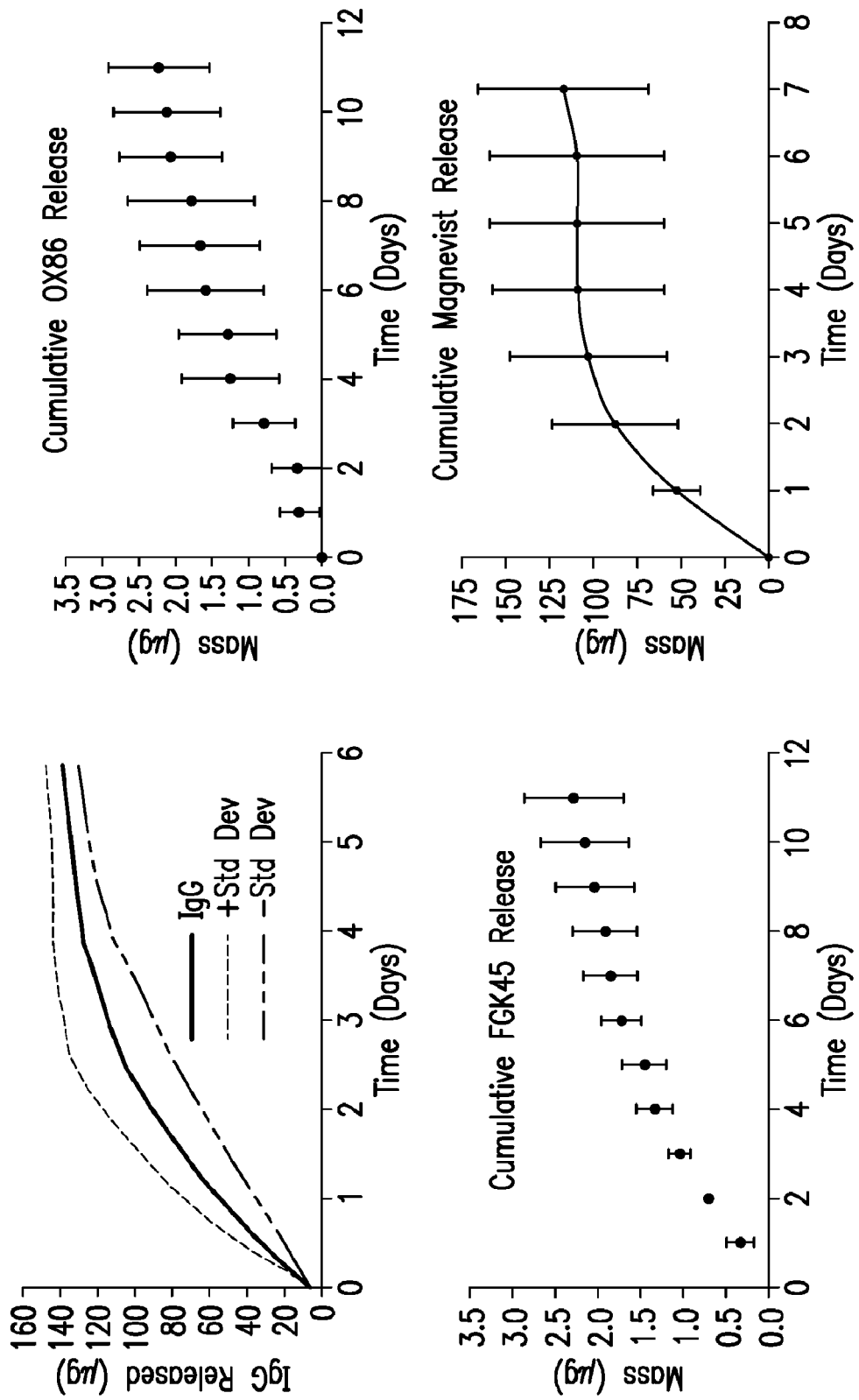
FIG. 5 is a group of graphs showing the sustained release of IgG, OX86, FGK45 and gadopentetate dimeglumine from Bayer (available under the trademark, Magnevist®, and referred to Magnevist in this document) from drug eluting fiducial markers.
Figure 6:
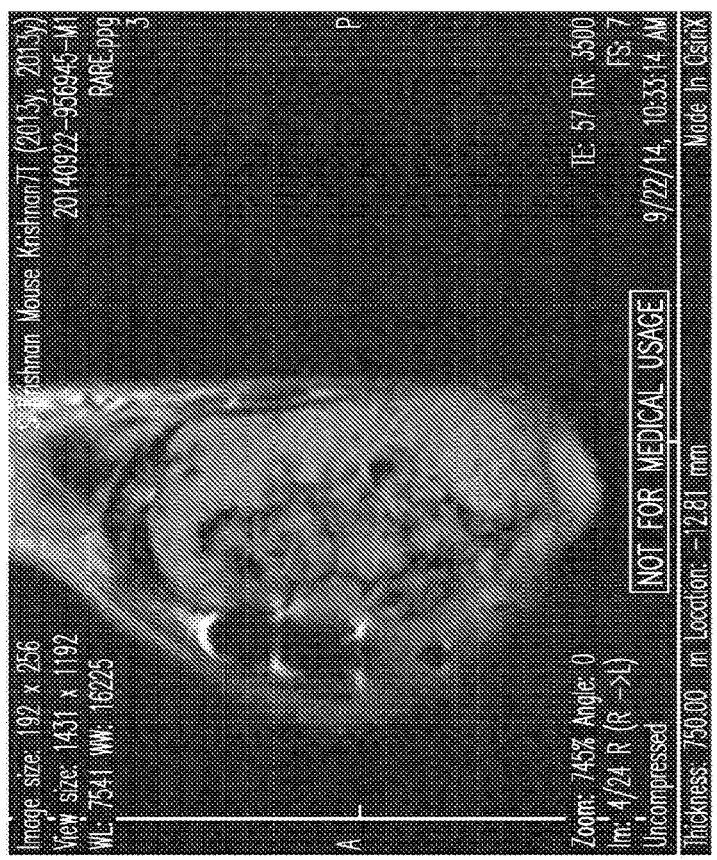
FIG. 6 shows a PEEK drug eluting fiducial marker releasing Magnevist intratumorally. High Magnevist concentration inside the implant had an undetectably fast T1 relaxation time, causing it to appear as a void.
Figure 6:
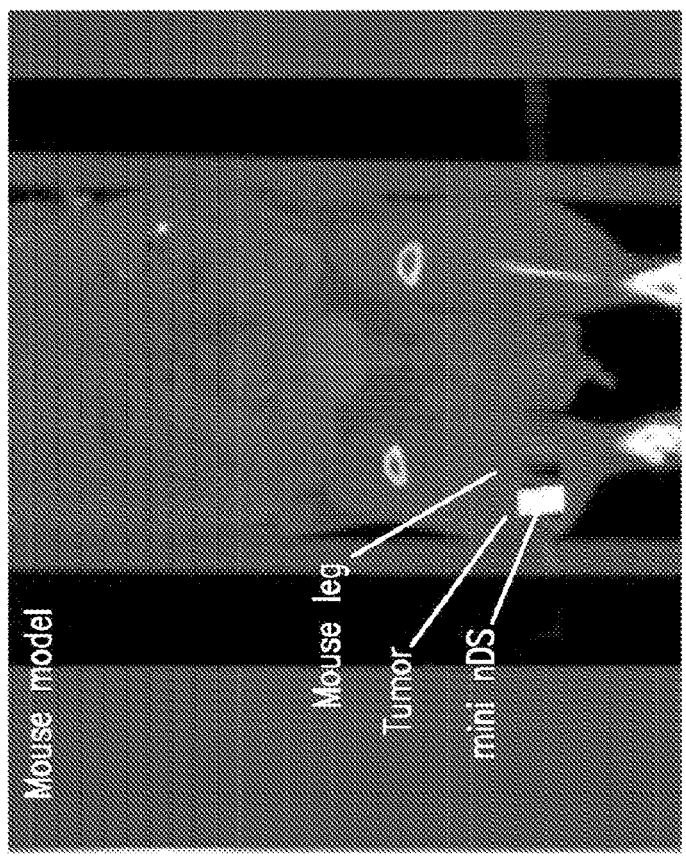

Once fabricated, nanofluidic membranes with 20 nm nanochannels on $6.0 \times 6.0 \times 0.70$ mm$^3$ silicon chips were subdivided with an ADT 7100 precision dicing saw (Advanced Dicing Technologies, Ltd., Yokneam, Israel) into squares approximately $0.75 \times 0.75 \times 0.70$ mm$^3$. Scanning electron microscopy (SEM) images of the membranes before and after sectioning are shown in FIGS. 4A and 4B. The diced chips were piranha washed in 70% $S_2O_4$ and 30% $H_2O_2$, inserted within the end of 3 mm tubes made of either 18 G 316 stainless steel (McMaster-Carr, Atlanta, GA) or PEEK (IDEX Health and Science, Oak Harbor, WA), and epoxied into place. The tubes acted as system casings and drug reservoirs. The various tubing materials were selected to be complementary with different imaging modalities. Stainless steel capsules offered high X-ray computed tomography (CT) contrast, while the PEEK capsules were compatible with magnetic resonance imaging (MRI) and utilized in this study for the release and detection of Magnevist (Bayer, Leverkusen, Germany). The second end of each tube was sealed with silicon adhesive (Nusil, Carpinteria, CA) to provide a resealable access point for drug loading. Images of assembled nanochannel implants are shown in FIGS. 2A-2D. As the implants were approximately 3.5 mm long with a silicone cap at one end and a semi-hollow membrane set at the other, they presented a reservoir capacity of 2.5-3 μl. Drugs were loaded manually through the silicon caps with a 32 G syringe needle. A second needle was inserted into the interior reservoir space through the silicon cap to allow venting during filling. Nanochannel capsules were weighed before and after the loading process to ensure proper dosage.

The drug eluting fiducial markers were loaded with a number of different molecules to examine release kinetics into simulated physiological solution in vitro. In a series of experiments, the implants were loaded with ~2.5 μL of OX86, FGK45, or Magnevist, placed in a 70 μL cuvette, and immersed in PBS. The cuvettes were sealed with tight-fitting lids and kept in an incubator at 37° C. The PBS solution was sampled and replaced daily. The OX86 and FGK45 release was quantified by micro-BCA assay (Sigma-Aldrich). The Magnevist was quantified through MR scanning. (7 T magnet, cut-down 96-well plate in a wrist coil). An additional experiment for quantifying IgG release was conducted similarly, but at room temperature and quantified via UV-Vis spectroscopy at 280 nm sampled every 10 minutes.

In Vitro Testing

The drug eluting fiducial markers were implanted into murine melanomas through a percutaneous approach in keeping with an approved IACUC protocol. Melanomas were induced in the right hind thigh of C57BL/6 mice through subcutaneous injection. Once tumors reach 1 cm in diameter, drug eluting fiducial markers loaded with Magnevist were loaded into beveled, 13 G needles for implantation. The needle was used to pierce the skin and tumor prior to miniature devices extrusion (one per mouse) into the malignancies' interiors. Stainless steel drug eluting fiducial markers were imaged with CT, demonstrating their usefulness as radio-fiducials. PEEK drug eluting fiducial markers were scanned at 3 and 7 days post-implantation to track Magnevist release.

Solution Preparation

Solutions of 150 kDa rat anti-mouse OX86 (BioX Cell, West Lebanon, NH) and FGK45 (Miltenyi Biotec, Bergisch Gladbach, Germany) were purchased from their manufacturers and maintained at 4° C. prior to loading within the nanochannel capsules. The hydrodynamic radius for Immunoglobulin G was found to be 6.4 nm from a website called BioNumbers. Loading concentrations were 1.386 and 2 mg/ml for OX86 and FGK45, respectively. Standard curves were prepared by serial dilution. Doxorubicin hydrochloride salt (LC Laboratories, Woburn, MA) was obtained as a dry powder at 579.98 kDA and stored at room temperatures. The predicted hydrodynamic radius for Doxorubicin is 2.6 nm. This radius was calculated using the Stokes-Einstein equation, where the dynamic viscosity of water was assumed to be 0.933 mPa*s, and the diffusion coefficient was found in a paper written by Weinberg et al. A loading solution of 0.58 mg/ml was created through weighing the requisite mass on an analytical balance and resuspension in Millipore water. Standard curves were prepared identically. Magnevist (add make/model), at 938 kDa, was obtained in solution at a concentration of approximately 470 mg/ml and maintained at room temperature. The hydrodynamic radius for Magnevist was predicted to be 1.5 nm using the same method as that of Doxorubicin. The dynamic viscosity of phosphate buffered saline solution (PBS) was assumed to be 0.7 mPa*s, and the diffusion coefficient was found in a paper written by Gillis et al. Loading solution concentration was 47 and 470 mg/ml for the in vitro and in vivo experiments, respectively.

Doxorubicin Release In Vitro

Doxorubicin loaded nanochannel capsules (n=5) were immersed in 400 µl of Millipore water in microvolume spectroscopy cuvettes sealed with tight-fitting lids. Absorbance measures were taken every 10 min for 9 days at 479 nm by a custom-built robotic carousel (Quantum Northwest, Inc.) connected to a UV-Vis spectrophotometer (Cary 50, Agilent Technologies, Inc.). The 479 nm wavelength was selected as optimal for doxorubicin with this system by prior full spectrum analysis. The cuvettes were maintained at 23±0.3° C. for the duration of the experiment. Data were normalized with respect to a Millipore water blank, and the cumulative release of the agents was obtained through comparison to a standard curve.

Monoclonal Antibody Release In Vitro

OX86 and FGK45 loaded nanochannel capsules (n=4) were immersed in 200 µl of PBS in microvolume cuvettes sealed with tight-fitting lids. The cuvettes were maintained in a 37° C. incubator for 12 days. The 200 µl of sink solution was removed and replaced each day with fresh PBS. The removed samples were at 4° C. Antibody release in the daily samples was quantified via a µBCA assay (Thermo Scientific, Grand Island, NY). Briefly, 150 µl of each sample was mixed with an equal volume of reagents in a 96 well microvolume plate. After incubation at 37° C. for 2 hours, the plate was read using a Synergy H4 Hybrid Reader (BioTek Instruments, Inc., Winooski, VT) at a wavelength of 562 nm. Protein concentration values were calculated through comparison to a serially diluted bovine serum albumin (BSA) standard packaged with the kit.

Magnevist Release In Vitro

PEEK nanochannel capsules loaded with Magnevist (n=4) were immersed in 500 µl of PBS in microvolume cuvettes sealed with tight-fitting lids. These microvolume cuvettes were then placed in a 37° C. incubator. The 500 µl of sink solution were sampled and replaced daily for 7 days. The sink samples were stored at 4° C. Magnevist concentration within the samples was quantified through MR imaging of the samples within a custom-built 49 well plate (7×7) with 300 µl well volumes. T1 mapes were acquired on a clinical-grade, 3 T MRI Scanner using the inversion recovery method with five inversion times (Ingenia, Philips, Best, The Netherlands). Acquisition parameters for the scans are summarized in Table 1. Postprocessing and concentration determination via the linear relationship between T1 and contrast agent concentration were carried out using MATLAB (MATLAB 8.4, MathWorks, Inc., Natick, MA, USA).

TABLE 1

MRI acquisition parameters for in vitro Magnevist release.

| | TR (ms) | TR (ms) | TE (ms) | ETL | Averages | In-Plane Resolution (mm) | Slice Thickness (mm) | TI (ms) |
|---|---|---|---|---|---|---|---|---|
| T1W | 5250 | 7.6 | 5250 | 4 | 1 | 0.5 | 1 | 26-5000 |

Intratumoral Magnevist Release

All animal procedures described herein followed IACUC protocols approved by their requisite institutions. C57B16 mice were implanted with $10^6$ melanoma cells (B16F10) in the upper thigh (n=5). Once tumors reached 12 mm in its longer axis, sterile nanochannel implants loaded with 470 mg/ml of Magnevist were percutaneously implanted into the tumors with a 15 G, percutaneous trocar at a 90°angle from the axial axis of the tumor. Briefly, rodents were anesthetized with 3% isofluorane and immobilized within a sterile field. The percutaneous implantation site was cleaned with chlorhexidine and 70% ethanol and all nearby hair was shaved. The trocar was inserted to the target depth of approximately 5 mm. The nanochannel capsule was extruded through manual pressure with the obturator and the trocar was removed. A single drop of bupivicaine was added to the implantation site. The implantation site was closed with suture to ensure implant immobility and restrict animal agitation of the site. The mice had secondary heating maintained throughout the procedure and until they recovered from anesthesia.

MR Acquisition and Analysis

For the in vivo MR imaging, T1- and T2-weighted images were acquired axially with respect to the laboratory frame of reference on a 7 T Bruker BioSpec Scanner (Bruker Biospin, Billerica, MA, USA). Acquisition parameters for the scans are summarized in Table 2. Maximum image projection (MIP) images were reconstructed from T1-weighted images and oriented axially with respect to the axes of the implant to measure the enhancing volume at both timepoints. Volumes were estimated via manual length and cross-sectional area measurements of the enhancing region on the MIP images using OsiriX Dicom Viewer 5.8.2. (Pixmeo, Geneva, Switzerland).

TABLE 2

MRI acquisition parameters for in vivo Magnevist release.

|  | TR (ms) | TE (ms) | ETL | Average | In-Plane Resolution (mm) | Slice Thickness (mm) | Slice Gap (mm) |
|---|---|---|---|---|---|---|---|
| T1W | 900 | 9.5 | 1 | 2 | 0.16 | 0.75 | 1 |
| T2W | 3500 | 57 | 12 | 4 | 0.16 | 0.75 | 1 |

CT Imaging and Analysis

Xenograft models of prostate cancer were grown in Foxn1Nu animals by implanting $2\times10^6$ PC3 cells obtained from the American Tissue Culture Collection in the upper thigh of each mouse (n=6). Tumor growth was monitored with the aid of an ultrasound system (VevoLZ, Visiotronix Inc.) to identify transition to the necrotic stage. Before necrosis and once tumors reached 12 mm in the longer axis, sterile nanochannel implants loaded with PBS were percutaneously implanted into the tumors with a 15 G, percutaneous trocar at a 90° angle from the axial axis of the tumor. Anesthesia and post-implantation treatment were identical to above. One week after implantation, animals were submitted to inhaling anesthesia (Isoflurane/$O_2$ 15%), and tumors were imaged in a XRAD small animal dedicated X-ray Computed Tomography (CT) irradiator (40 kVp, 5 mAs, $0.25\times0.25\times0.5$ mm$^3$ voxel resolution). Image post-processing was conducted with OsiriX Dicom Viewer 5.8.2.

Intratumoral Delivery of IgG Tagged with Alexa Fluor

Xenograft models of human pancreatic cancer were grown in Fox1$^{Nu}$ animals by implanting PANC-1 cells obtained from the ATCC in the upper thigh of each mouse (n=3). Tumor growth was monitored via caliper measurement. Once tumors reached 10 mm in the long axis, sterile nanochannel implants loaded with goat anti-mouse IgG (H+L) non-specific antibody conjugated with Alexa Fluor 488 (Invitrogen) were percutaneously implanted into the tumors as previously described. Buprenorphine 0.05% was used for maintaining analgesia. Five days after implantation, the mice were humanely euthanized. The tumors were excised, fixed in 10% formalin, and embedded in paraffin. Starting at the tumor periphery estimated to be nearest the releasing end of the implant, serial sections of 8 micron thickness at 15 micron intervals were cut with a microtome (RM2235, Leica Biosystems, Buffalo Grove, IL) until the implant body was encountered. The sections were imaged with an ImageXpress Micro High Content Screening System (Molecular Devices LLC, Sunnyvale, CA). Images were acquired at a 10× magnification.

In Vitro Antibody Release

Figure 7:
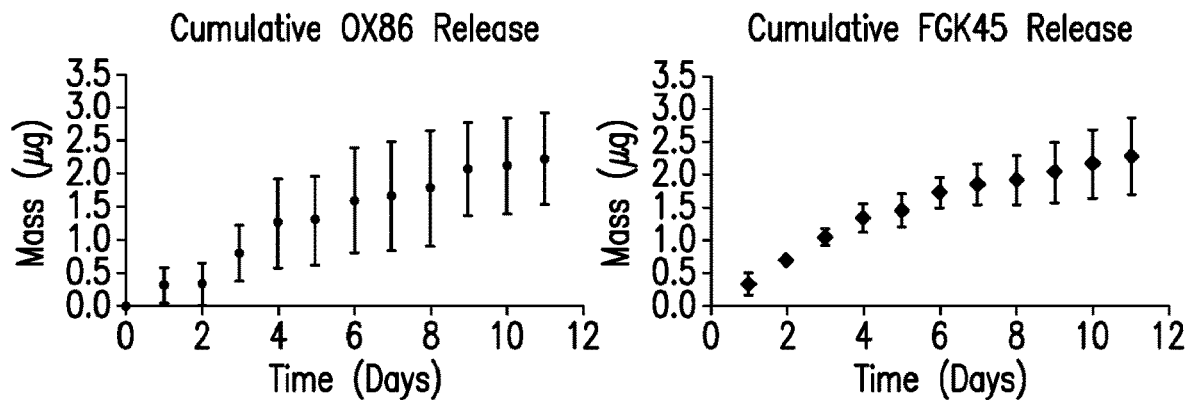
FIG. 7 is a pair of graphs showing mean cumulative release of the monoclonal antibodies OX86 (left) and FGK45 (right) (n=4) from the nanochannel implants in vitro.

The nanochannel capsules were loaded with OX86 or FGK45 and placed in isotonic conditions in vitro to characterize their release kinetics. Diffusive release of OX86 and FGK45 was determined by immersing loaded nanochannel capsules in PBS within microvolume cuvettes. The cuvettes were sealed with tight-fitting lids and maintained at 37° C. for the duration of the experiment. Fluid samples of the PBS sink solution were collected daily and the concentration of released antibodies was quantified through µBCA assay. FIG. 7 exhibits the release rates determined for OX86 and FGK45 through µBCA assay.

This experiment demonstrated sustained monoclonal antibody release over a period of several days. These antibodies are both IgG isotypes with similar molecular weights and hydrodynamic radii. This gave rise to their notably similar diffusive release kinetics. Their cumulative release follows a bi-phasic linear profile, more apparent for the FGK45, that has been previously identified with some proteins such as bovine serum albumin (D. Fine, et al., *Lab Chip*. 10, 3074-83 (2010)). In addition, the release seemed to be within a reasonable range for physiological efficacy. Intratumoral immunomodulatory studies have employed monoclonal antibody injections of 50 to 250 µg over a course of multiple injections, utilizing dosage levels similar to systemic administration (M. Gerloni, et al., *Proc Natl Acad Sci USA*. 97, 13269-74 (2000); S. Piconese, et al., *J Exp Med*. 205, 825-39 (2008); M. Chonan, et al., *Neuro Oncol*. (2015)). However, Marabelle et al. demonstrated that using 100× fewer antibodies (OX86 and anti-CTLA4 in their study) would have the same effect if injected intratumorally (A. Marabelle, et al., *J Clin Invest*. 123, 2447 (2013)). The release demonstrated from the disclosed nanochannel capsules were within this range, which can be further increased by designing the system with a larger reservoir, larger nanochannels, or a more concentrated formulation. Furthermore, Marabelle et al. observed that the antibodies were rapidly cleared from the local area, reaching undetectable levels within 72 hours. Taken together, these results indicate that the disclosed device can be able to provide clinically relevant amounts of these antibodies for a sustained period substantially longer than intratumoral injection, which motivates further development for immunotherapy and vaccine delivery.

Doxorubicin Release

The nanochannel capsules were loaded with Doxorubicin and placed in isotonic conditions in vitro to characterize their release kinetics. The nanochannel capsules were immersed in PBS within microvolume cuvettes, which were sealed with tight-fitting lids. Release into the sink solution was measured via absorbance measurements at 479 nm by a robotic 48-cell carousel (Quantum Northwest, Inc.) linked to a UV-Vis Spectrophotometer (Cary 50, Agilent Technologies, Inc.). Overall drug release was evaluated via comparison of measured absorbances to standard curves following normalization with respect to initial conditions (t=0). FIG. 8 exhibits the release rates determined for Doxorubicin.

This experiment showed release of doxorubicin at doses capable of providing local therapeutic and radiosensitizing effects (M. S. Lesniak, et al., *Anticancer Res*. 25, 3825-3831 (2005)). Doxorubicin is an anthracycline antibiotic used to treat a diverse set of cancers through DNA intercalation, frequently as part of a combinatorial therapy (R. Z. Orlowski, et al., *J Clinical Oncology*. 25, 3892-3901 (2007)). Doxorubicin carries a positive charge at physiological pH, which will theoretically define its transport and distribution within the nanochannel to follow the "near-surface diffusion" profile posited by Grattoni et al. (*ACS Nano*. 5, 9382-9391 (2011)). Briefly, this refers to the attraction of cationic molecules in solution to the negatively-charged silicon walls of the nanochannel at near neutral pH. This results in local ion concentration near the nanochannel wall. The thickness of this layer is dictated by the electrical double layer. In this experiment, release depleted around 80% of the reservoir volume in 4 days, reaching a plateau well before the antibodies, which did not plateau in the timeframe studied. This faster rate of achieving steady state was expected, as the Stokes radius for Doxorubicin can be calculated to be between 2 and 3 nm, contrasting with the approximately 6.4 nm radii for IgG isotype immunoproteins (R. Milo, et al., *Nucleic Acids Res*. 38, D750-D753 (2010)).

While intuitive as Fickian diffusion has an inverse relationship with hydrodynamic radius, this has also been previously demonstrated with similar silicon membranes by this group (S. Ferrati, et al., *J Control Release*. 172, 1011-9 (2013)).

Although doxorubicin has demonstrated efficacy in a number of different malignancies, common toxic reactions to systemic administration at therapeutic dosages include myelosuppression, alopecia, diarrhea, and host of different irritations and inflammations, in addition to more serious reactions such as cardiomyopathy (B. Kalyanaraman, et al., in Oxygen/Nitrogen Radicals: Cell Injury and Disease, Springer, (2002)). Local delivery could enhance concentration within target volumes while lowering overall dose, reducing the potential for such complications. This is further evidenced in the work of other groups, who are developing liposomal and nanocarrier methods to localize and target doxorubicin release to reduce systemic toxicities (R. Panchuk, et al., *J Biomed Nanotech*. 11, 1139-1152 (2015); S. Mitra, et al., *J Controlled Release*. 74, 317-323 (2001); A. Hekmat, et al., *J Biomed Nanotech*. 8, 968-982 (2012)). It should be noted the nanochannels can be sized to work synergistically with carrier molecules. While directly effective as a chemotherapeutic, combinatorial delivery of doxorubicin with immunomodulators, followed by subsequent radiotherapy, could enhance therapeutic potential.

Intratumoral Radiofiducial

Intratumoral implantation within mouse xenograft models of pancreatic cancer enabled assessment of the stainless steel nanochannel implant's capability as a radiofiducial. Tumors were implanted with nanochannel capsules via percutaneous, trocar delivery once the masses reach 12 mm on their long axis, fiducial implantations were performed in each mouse as a survival surgical procedure. CT images are shown in FIGS. 9A and 9B.

The radiological CT image shown in FIGS. 9A and 9B supports the clinical use of the nanochannel capsules as fiducials as minimal artifact at the implant site was observed. Moreover, the fiducial can be clearly seen in the X-ray CT without significantly compromising contrast in the soft-tissues or resolution between the organs. The—somewhat surprising—bone-matching density level of the fiducial allows for its precise localization with the simple use of an X-ray image. Anatomical features shown in the CT provide physical reference for localization and dimensions of the implant. In the image, two elliptical hips and ankle joints illustrate the small dimensions considered in the study.

In Vitro Magnevist Release

The nanochannel membranes integrated with PEEK capsules were loaded with 47 mg/ml Magnevist solution and immersed in 500 µl of PBS within a sealed microcuvette. Fluid was sampled and replaced daily for the experiment's duration. MR measured Magnevist release from nanochannel capsules in vitro is shown in FIG. 10.

Magnevist release was relatively rapid for the first 2 days and began to plateau by Day 3. Similar to the other molecules in this study, a biphasic linear release was observed. Approximations based on loading concentration predict that this correlates with 85% of the loaded Magnevist having been released. The hydrodynamic radius for Magnevist was estimated to be 1.5 nm, which can explain the slightly faster release relative to doxorubicin. Increasing or decreasing the release timeframe could be attained through modifying the reservoir capacity or size of the nanochannels, as the fabrication process has been demonstrated capable of creating nanochannels sized to application down to 2.5 nm in height. Previous studies incorporating substantially larger membranes and reservoirs for attaining clinically relevant systemic delivery have exhibited zero-order release for multiple months. Modifying this device to achieve a longer release timeframe can be desirable in studying modulation of interstitial clearance and diffusion patterns within progressing tumor models over several weeks.

Intratumoral Magnevist Release

Utilizing the percutaneous trocar delivery approach described above, PEEK nanochannel implants loaded with Magnevist were inserted intratumorally into the upper thigh of C57B16 mice with induced melanoma. T1- and T2-weighted images of the site 1 day after implantation are shown in FIG. 11-11C. The implants were visualized on T1-weighted images as an area of hypointensity corresponding to the PEEK body and surrounded by a hyperintense halo of contrast agent (FIG. 11B). Implant location could also be identified on T2-weighted images that, in addition, highlighted tumor heterogeneity (FIG. 11A). The average enhancing volume was found to be 75±25 mm$^3$ on day 1 and 65±13 mm$^3$ on day 3, implying substantial local clearance and similar release kinetics occurring as were observed for the Magnevist release in vitro.

PEEK implants demonstrated release over days. MR timepoints were chosen based on the in vitro experiments, which exhibited rapid release for the first 2 days with substantial decrease on day 3 as evident in FIG. 10. The lesser enhancement volume demonstrates that the Magnevist was cleared from the immediate tumor vicinity of the implant. An unexpected outcome was the implant's loaded concentration being too high for visualization, as the relaxation time was faster than the scanner could detect. This is further evidenced by the sharp onset of observable enhancement a few mm from the implant's exterior. The narrow band of this observable enhancement, beginning 2-5 mm from the implant's exterior and approximately 1 mm thick, provides evidence of rapid clearance of the contrast agent from the tumor tissue. FIG. 11C serves as an idealized graphical representation of the relationship between the normalized concentration and the visible contrast zone.

Intratumoral Delivery of IgG Tagged with Alexa Fluor

The paraffin embedded PANC-1 tumors were carefully sectioned to expose the tissue nearest the implant's nanochannel membrane. Starting at the tumor periphery estimated to be closest to the membrane, serial sections of 8 micron thickness at 15 intervals were cut with a microtome until the implant body was encountered. The sections were stained with hematoxylin and eosin (H&E) prior to imaging with an ImageXpress Micro High Content Screening System (Molecular Devices LLC, Sunnyvale, CA). Both fluorescent and brightfield images were acquired at a 10× magnification and stitched together with the onboard proprietary software as shown in FIGS. 12A and 12B.

The IgG secondary antibody used in this experiment had a highly similar molecular weight and structure to the OX86 and FGK45, implying that it would have a highly similar diffusive release profile. However, the different binding specificities leave it only an estimate of how these antibodies would localize in vivo. Comparison of fluorescent signal in untreated control slides provided confidence that the signal here is not attributable to auto-fluorescence. Like the Magnevist release experiments, a region of high signal is observable within 1-4 mm of the implant. Limited fluorescence is evident within the tumor tissue, although signal is observable in the dermal tissue several millimeters away from the implant location, suggesting broad distribution of the releasate. The nanochannel end of the implant seems to have overpenetrated the malignant tissue, leaving the final placement within skeletal muscle. This is perhaps attributable to the density and hardness of the tumor. The poor distribution within the malignant areas can be attributable to the densely packed cells and heightened intratumoral pressure typical of pancreatic tumors. As the immunotherapeutic approach does not necessarily require substantial infiltration of the tumor, this is not a discouraging result. However, steps could be taken to enhance penetration if desired, such as co-delivering the antifibrotic Losartan or another permeabilizing drug (B. Diop-Frimpong, et al., *Proc Natl Acad Sci USA*. 108, 2909-2914 (2011)); I. Fuso Nerini, et al., *Clinical Pharmacol Therapeutics*. 96, 224-238 (2014)). It would be highly interesting to look at how the tissue penetration is affected by different therapeutic approaches and whether this device platform could be used as a metric for characterizing and understanding developing malignancies.

Successful delivery of this variety of different molecules demonstrates the wide versatility and utility of this implantable nanochannel system capable of sustained delivery over several days. In vitro experiments showed release of chemotherapeutics and radiosensitizers, immunomodulators, and image contrast agents. In vivo experiments demonstrated the implant's minimally-invasive deployment, intratumoral delivery of antibodies and contrast agents, and synergistic utility with CT and MR imaging. It is important to note that the implants were well-tolerated without abnormal wound healing or adverse immune reactions being observed.

The implant benefits from a simple architecture that can be re-designed and re-engineered to application. The nanochannels can be fabricated with varying height and channel density, enabling tuning to fit a given molecule and desired dose release rate. As the nanochannel membranes themselves can be mass produced using well-understood fabrication techniques refined by the semiconductor industry and the other components are low cost, commercialization should lead to an inexpensive device. The small volume of each individual implant alleviates concerns of toxic reactions if an implant should be breached during implantation, although the robustness of the components should limit the possibility of such an occurrence. Limitations of the current design include the restricted reservoir capacity and the probable requirement for the implants to be permanent. The latter is a typically endured drawback considered clinically acceptable in many interventional therapeutic approaches, such as brachytherapy 37. Future development will include designing a biodegradable variant of the platform, capable of breaking down into non-toxic components that can be safely resorbed by the body in the months after release has ceased.

Immunotherapy and Radiotherapy

This example determined if any abscopal activity could be induced with nDSmini+radiotherapy (RT) and whether the tumors would respond to the dual treatment (FIG. 13). The tumors were induced bilaterally in both rear thighs through injection of approximately $10^6$ PANC-1 cells into C57Bl/6 mice. There were 4 groups: nDSmini loaded with PBS, RT only, nDSmini loaded with OX86+FGK45, and RT+nDSmini loaded with OX86+FGK45. The n-number breakdown is shown in Table 3. The treatment nDSmini were loaded with a mixture of OX86 and FGK45 (anti-OX40 and anti-CD40, 3 microliters at ~2 mg/ml each). Once at least one of the tumors in each mouse reached 10 mm in its largest dimension, the control and treatment nDSmini were implanted intratumorally through a 15 G trocar into the larger tumor (Groups 1, 3-4). Three days after implantation, the same larger tumor site was irradiated with 10 Gy of ionizing radiation (Groups 2 and 4). Due to undue tumor burden after 7 days, the animals were euthanized. Fluorescence-activated cell sorting analysis (FACS) of the splenocyte population (FIGS. 14A and 14B) exhibited a down-regulation of CD4+ cells (associated with T-regulatory cells) and an up-regulation of the CD8+ marker (associated with macrophages), providing some evidence of systemic abscopal activity.

TABLE 3

Treatment groups for immunotherapy efficacy study

| Group | Treatment | n |
|---|---|---|
| 1 | $nDS_{mini}$ | 1 |
| 2 | RT | 1 |
| 3 | $nDS_{mini}$-OX86 + FGK45 | 2 |
| 4 | RT + $nDS_{mini}$-OX86 + FGK45 | 2 |

Ocular nDSmini (nDSμ)

A device was developed wherein the macrochannel side of the 2×2 diced silicon membranes was packed directly with powdered drug or contrast agent (FIGS. 15A-15C). After loading, the macrochannel was sealed with UV curable epoxy. The nearly cubical device (approximately 0.7×0.7× 0.8 mm) could then be placed in aqueous solution, where capillary filling of the micro- and nanochannels would wet the system and powder, allowing diffusive release. In vitro releases of several ocular-related drugs have been conducted, including 5-aminosalyscilic acid, bimatoprost, and timolol maleate, as shown in FIGS. 16A-16C. These experiments were conducted in 550 μl (5-aminosalicylic acid and bimatoprost) or 3 ml cuvettes (timolol maleate) monitored by a UV-Vis spectrometer every 10 minutes for the duration of each release.

The next steps can include integration within a polymeric, episcleral device. This device can be between 0.5 and 1 mm in height. To achieve this, the nanochannel membranes can be lapped pre- or post-dicing into 2×2 subsections to a 0.5 mm height. This device can be tested in a phantom optimized for transscleral drug delivery prior to in vivo deployment.

Breast Cancer Treatment Thorough nDSmini Delivered Exosome Nanocarriers

Therapeutic options for Triple Negative Breast Cancers (TNBC) patients are limited to a chemotherapy regimen typically inclusive of doxorubicin due to the lack of therapeutically targetable markers. Conventional systemic chemotherapy results in adverse systemic toxicity, immunosuppression, and insufficient tumor uptake, thus overshadowing the apparent cytotoxic benefit of chemotherapy. As such, chemotherapeutic delivery strategy remains an enduring clinical challenge in TNBC.

Doxorubicin-loaded dexosomes delivered intratumorally via a nanofluidic Delivery System (nDSmini) can permit controlled tumor-targeted chemotherapeutic delivery and concurrently enhance anti-tumor immune response, leading to improved TNBC outcome. Autologous dexosomes (exosomes from dendritic cells) as secondary carriers of doxorubicin can be used to enhance tumor cell uptake through its inherent propensity to unload cargo into neighboring cells, 2) tumor-targeted localized chemotherapy delivery via intratumoral implantation of the disclosed nDSmini drug delivery system for prolonged tumor exposure to chemotherapy, and 3) potentiation of anti-tumor immune response through the exploitation of the intrinsic nature of dexosomes to present antigens and activate T cells and natural killer cells.

The disclosed intratumoral nanofluidic-mediated chemotherapy delivery system coupled with dexosomes can function as both a drug delivery vehicle and immune stimulant for TNBC, and other cancers. The nDSmini intratumoral implant can facilitate localized and prolonged drug delivery at potent concentrations, eliminating the need of intravenous catherization, pumps, or ports associated with other drug delivery systems for drug infusion.

Photoacoustic Imaging of nDSminis

Photoacoustic (PA) imaging (also known as optoacoustic imaging) can be used to image the disclosed nDSmini. While available MR and US imaging systems have resolutions on the order of millimeters, PA imaging is able to resolve structures with dimensions of 150 microns centimeters deep in living tissue. In addition, PA imaging has been demonstrated to provide high fidelity contrast agent visualization in vivo, potentially enabling its employment to image both the nDSmini and releasing agents. Unloaded PEEK (P) and stainless steel (SS) nDSmini were imaged in a transparent tissue phantom gelatin with US and PA imaging, as shown in FIGS. 17A-17C.

In addition, US and PA scans of an SS nDSmini in a phantom mimicking both the optical and acoustic properties of human tissue (in the relevant optical and acoustic spectra) were captured. The nDSmini was cast at a depth of 1.4 cm into the phantom. A representative image is shown below in FIG. 18A. The spectral response of the SS nDSmini is shown in FIG. 18B.

Breast Cancer Treatment

Luciferase expressing 4T1 mouse mammary gland carcinoma in Balc/c mice with nDSmini-delivered OX86 and FGK45 can be performed. The two monoclonal antibodies delivered, OX86 and FGK45 (anti-OX40 and anti-CD40), can serve to stimulate local immune response within an orthotropic breast cancer model, causing regression of the tumor. These antibodies can be solubilized in aqueous solutions and delivered over a 2 week period.

1×1 nDSmini Variant

The diameter of the nDSmini is dependent on the width of the diced, 2×2 membranes. This can been problematic for some trocar deliveries in mice, as the trocar must be 15 G to accommodate the tightfitting 17 G tube that is the case and reservoir for the nDSmini. To overcome this, precision dicing techniques were successfully employed to produce a 1×1 functional subunit of the nanochannel membranes. This enabled the creation of nDSmini half the diameter of previous, which fit into an 18 G, stainless steel tube. Still under active development, the 1×1 variant should have 25% of the release rate and volume capacity per unit length relative to the 2×2. Images of the 1×1 and 2×2 diced membranes and the fabricated nDSmini devices are shown in FIGS. 19A and 19B.

The devices, methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. An implantable intratumoral device, comprising: a tubular body defining a first opening and a reservoir containing an immunotherapeutic agent, and a nanochanneled membrane disposed within the first opening, wherein the tubular body has a length of less than 5 mm.

2. The device of claim 1, wherein the nanochanneled membrane comprises nanochannels from 2.5 nm to 100 nm in diameter.

3. The device of claim 1, wherein the nanochanneled membrane comprises nanochannels at a density of greater than 100,000 nanochannels $mm^{-2}$.

4. The device of claim 1, wherein the tubular body is titanium, tungsten, gold, or stainless steel.

5. The device of claim 1, wherein the tubular body has a diameter of less than 2 mm.

6. The device of claim 1, wherein the reservoir has volume from 0.5 µL to 10 µL.

7. The device of claim 1, wherein the tubular body defines a second opening, and the second opening is sealed with silicone, plastic, or rubber.

8. The device of claim 1, wherein the reservoir comprises a liquid or powder.

9. The device of claim 1, wherein the reservoir comprises an antibody or immunoglobulin.

10. The device of claim 1, wherein the reservoir comprises PD1, IgG, CTLA4, microRNA, PDL1, CD73, antiCD40 agonist, antiPD1 antibody, or pDox.

11. The device of claim 1, wherein the reservoir comprises one or more of OX86 and FGK45.

12. A method of treating a cancer, the method comprising: implanting into a tumor of a subject the implantable intratumoral device of claim 1.

13. The method of claim 12, further comprising:
monitoring the device radiographically during implantation, wherein the tubular body of the device is made of a radiopaque material.

14. The method of claim 12, wherein the cancer is rectal, cervical, lung, melanoma, prostate, or pancreatic cancer.

15. A method of collecting a sample from a subject, the method comprising: implanting into a tumor of a subject an implantable intratumoral device comprising a tubular body of a length of less than 5 mm and defining a first opening, a reservoir, and a nanochanneled membrane disposed within the first opening;
allowing interstitial fluid from the tumor to accumulate in the reservoir of the device:
withdrawing the device from the subject; and
isolating the interstitial fluid from the device, the interstitial fluid being the sample.

* * * * *